(12) United States Patent
Boffeli et al.

(10) Patent No.: US 11,839,383 B2
(45) Date of Patent: Dec. 12, 2023

(54) BONE DEFORMITY TREATMENT SYSTEM, DEVICE, AND RELATED METHODS

(71) Applicant: TRILLIANT SURGICAL, LLC, Houston, TX (US)

(72) Inventors: Troy J. Boffeli, Woodbury, MN (US); Shannon M. Rush, San Jose, CA (US); Michael Lee, Johnston, IA (US); Jordan Grossman, Akron, OH (US); Mark Hardy, Lakewood, OH (US); Graham Hamilton, Concord, CA (US); David Kawalik, Chandler, AZ (US)

(73) Assignee: TRILLIANT SURGICAL, LLC, Houston, TX (US)

( * ) Notice: Subject to any disclaimer, the term of this patent is extended or adjusted under 35 U.S.C. 154(b) by 274 days.

(21) Appl. No.: 17/335,403

(22) Filed: Jun. 1, 2021

(65) Prior Publication Data

US 2021/0369287 A1    Dec. 2, 2021

Related U.S. Application Data

(60) Provisional application No. 63/033,123, filed on Jun. 1, 2020.

(51) Int. Cl.
| | | |
|---|---|---|
| *A61B 17/15* | (2006.01) | |
| *A61B 17/80* | (2006.01) | |
| *A61B 17/56* | (2006.01) | |

(52) U.S. Cl.
CPC ........ *A61B 17/151* (2013.01); *A61B 17/8004* (2013.01); *A61B 17/8061* (2013.01); *A61B 17/8095* (2013.01); *A61B 2017/565* (2013.01)

(58) Field of Classification Search
CPC ... A61B 17/15; A61B 17/151; A61B 17/1775; A61B 2017/565; A61B 17/66; A61B 2017/681; A61B 17/8095; A61B 17/88; A61B 17/90; A61B 17/8061
See application file for complete search history.

(56) References Cited

U.S. PATENT DOCUMENTS

| | | | |
|---|---|---|---|
| 5,704,941 | A | 1/1998 | Jacober et al. |
| 6,030,391 | A * | 2/2000 | Brainard ................ A61B 17/15 |
| | | | 606/82 |
| 8,764,763 | B2 | 7/2014 | Kian-Ming et al. |
| 9,480,571 | B2 * | 11/2016 | McGinley ............. A61F 2/4202 |
| 9,888,950 | B2 * | 2/2018 | Perez ................. A61B 17/8085 |
| 9,936,994 | B2 | 4/2018 | Smith et al. |
| 9,936,995 | B2 | 4/2018 | Dacosta et al. |
| 10,045,807 | B2 | 8/2018 | Santrock et al. |
| 10,327,829 | B2 | 6/2019 | Dacosta et al. |
| 10,335,220 | B2 | 7/2019 | Smith et al. |
| 10,342,590 | B2 | 7/2019 | Bays et al. |
| 10,555,757 | B2 | 2/2020 | Dayton |
| 10,561,426 | B1 | 2/2020 | Dayton et al. |
| 10,575,862 | B2 | 3/2020 | Bays et al. |

(Continued)

*Primary Examiner* — Larry E Waggle, Jr.
(74) *Attorney, Agent, or Firm* — Veros Legal Solutions, LLP

(57) ABSTRACT

Bone deformity correction devices and methods of using such devices to correct bone deformities. The device can include an elongate body, an adjustable manipulation arm movably coupled to the elongate body, wherein the adjustable manipulation arm is configured to move axially and laterally, and a cutting guide removably attachable to the device elongate body.

16 Claims, 14 Drawing Sheets

(56) References Cited

U.S. PATENT DOCUMENTS

| | | |
|---|---|---|
| 10,603,046 B2 | 3/2020 | Dayton et al. |
| 10,610,241 B2 | 4/2020 | Wagner et al. |
| 10,729,453 B2 | 8/2020 | Woodard et al. |
| 2004/0122436 A1 | 6/2004 | Grimm |
| 2011/0264148 A1 | 10/2011 | Prandi et al. |
| 2013/0237989 A1 | 9/2013 | Bonutti |
| 2016/0015426 A1 | 1/2016 | Dayton |
| 2016/0235414 A1 | 8/2016 | Hatch et al. |
| 2018/0242987 A1 | 8/2018 | Lintula |
| 2018/0242988 A1 | 8/2018 | Dacosta et al. |
| 2018/0250024 A1 | 9/2018 | Woodard et al. |
| 2018/0280069 A1 | 10/2018 | Barmes et al. |
| 2018/0317992 A1 | 11/2018 | Santrock et al. |
| 2019/0125418 A1 | 5/2019 | Muller et al. |
| 2019/0133614 A1 | 5/2019 | Kian-Ming et al. |
| 2019/0274745 A1 | 9/2019 | Smith et al. |
| 2019/0307498 A1 | 10/2019 | Dacosta et al. |
| 2019/0328435 A1 | 10/2019 | Bays et al. |
| 2019/0328436 A1 | 10/2019 | Bays et al. |
| 2019/0336140 A1 | 11/2019 | Dacosta et al. |
| 2020/0015856 A1 | 1/2020 | Treace et al. |
| 2020/0093501 A1 | 3/2020 | Patel et al. |
| 2020/0014673 A1 | 5/2020 | Smith et al. |
| 2020/0155176 A1 | 5/2020 | Bays et al. |
| 2020/0155197 A1 | 5/2020 | Dayton et al. |
| 2020/0188003 A1 | 6/2020 | Schlotterback et al. |
| 2020/0197021 A1 | 6/2020 | Dayton et al. |
| 2020/0229828 A1 | 7/2020 | Wagner et al. |
| 2020/0253641 A1 | 8/2020 | Treace et al. |
| 2020/0028163 A1 | 9/2020 | Denham |
| 2021/0330311 A1* | 10/2021 | Denham ............... A61B 17/025 |
| 2021/0330335 A1* | 10/2021 | Boffeli .................. A61B 17/66 |

* cited by examiner

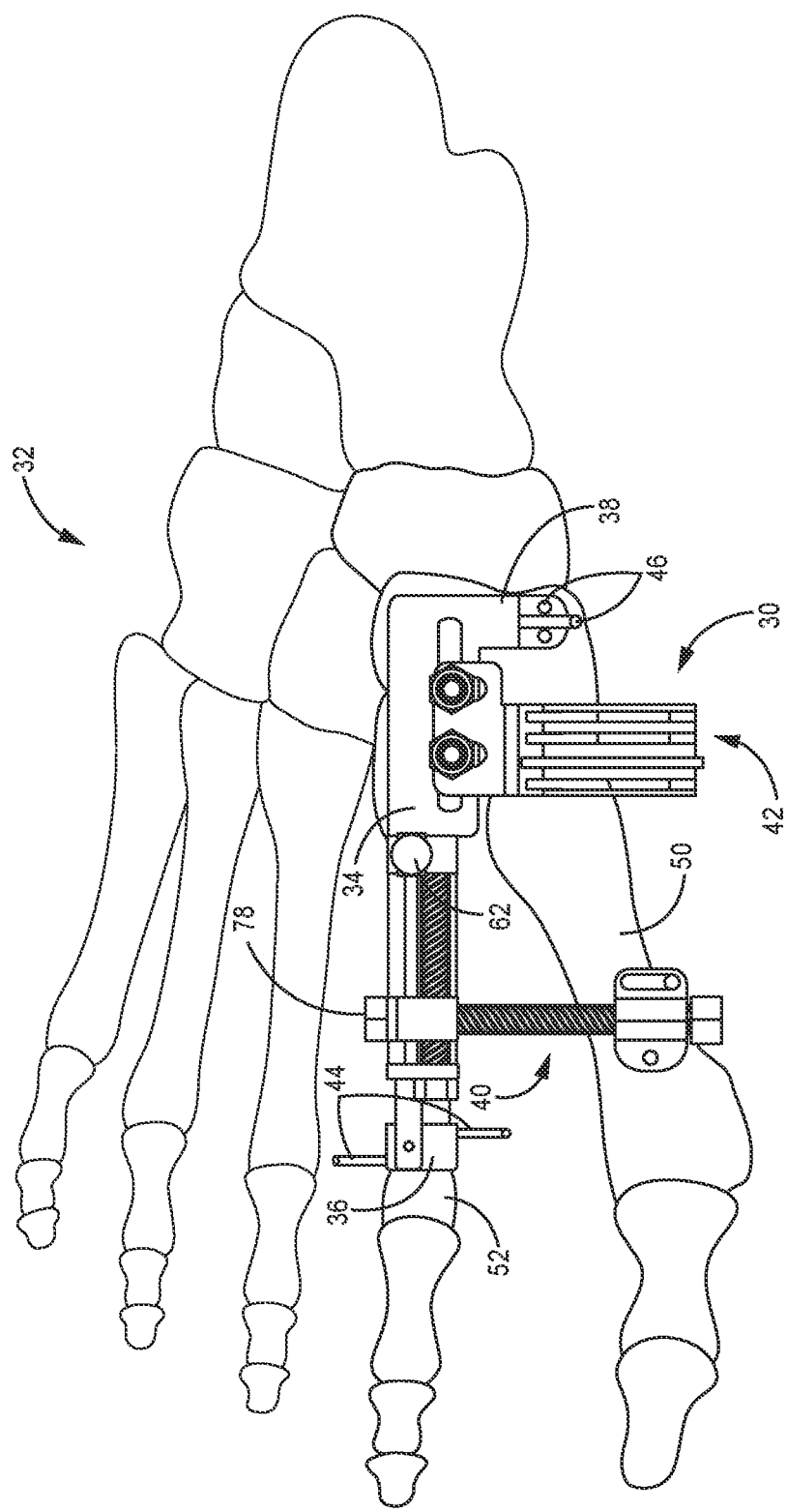

BONE DEFORMITY TREATMENT SYSTEM, DEVICE, AND RELATED METHODS

CROSS-REFERENCE TO RELATED APPLICATION(S)

This application claims the benefit under 35 U.S.C. § 119(e) to U.S. Provisional Application 63/033,123, filed Jun. 1, 2020 and entitled "Lapidus Fusion System, Device, and Related Methods," which is hereby incorporated herein by reference in its entirety.

FIELD

The various embodiments herein relate to bone deformity treatment systems and procedures, including, for example, Lapidus fusion treatment devices and procedures for treating hallux valgus, flatfoot deformity, cavus deformity, metatarsus adductus, midfoot arthritis, and other such bone deformities.

BACKGROUND

Lapidus fusion is a commonly performed procedure for various bone deformities, including, for example, hallux valgus, flatfoot deformity, cavus deformity, acute and chronic Lisfranc injury, midfoot arthritis, metatarsus adductus, and medial column insufficiency.

Lapidus fusion is a challenging procedure, especially when the surgeon is working without assistance. In known systems and procedures, there are generally many moving parts that require the surgeon to use multiple devices and both hands for the various steps.

One such example of a known procedure using known devices for treating hallux valgus is set forth in FIGS. 1A-1E. In this specific exemplary known procedure, the first step as best shown in FIG. 1A is the use of a positioning tool 10 that is used to perform a clamping action to urge the deformed first metatarsal 12 laterally into its natural (non-deformed) position, thereby correcting the deformity. Once the first metatarsal 12 is positioned as desired, the cutting guide 16 is positioned across the joint between the first metatarsal 12 and the medial cuneiform 14 bones and attached to both, as shown in FIG. 1B. Once the guide 16 is attached, a saw blade 18 is inserted through the slots in the guide 16 to resect a portion of each of the bones 12, 14. Once the resection is complete, the cutting guide 16 is removed and the compressor device 22 is attached, as best shown in FIG. 1O. The compressor device 22 is used to urge the first metatarsal 12 and the medial cuneiform 14 away from each other, thereby resulting in a gap 20 (also shown in FIG. 1O). The two portions of resected bone are then removed, and then the compressor device 22 is used to urge the two bones 12, 14 together. Once the two bones 12, 14 are urged together, a first fixation plate 24 is attached to the two bones 12, 14, as shown in FIG. 1D. Once the first fixation plate 24 is attached, the compressor device 22 is removed, and a second fixation plate 26 is attached as well, as shown in FIG. 1E. The second fixation plate 26 is attached such that it is parallel to the first fixation plate 24 with screws inserted at an approximately 90 degree angle to the screws of the first plate 26. This configuration strengthens the fixation of the two bones 12, 14 together. This completes the procedure.

As mentioned above, one disadvantage of these known procedures (including the exemplary procedure described above) is the number of different devices involved. And as each device is attached or otherwise used to perform the procedure, the surgeon must maintain the desired positioning of the various bones (as well as the devices), thereby requiring the use of at least the surgeon's two hands, and preferably the use of the hands of at least one assistant as well. Thus, another related disadvantage is the difficulty of maintaining the precision of the procedure given the various different devices involved and the difficulty of positioning each such device and maintaining that position.

Additional disadvantages relate to the fixation of the two known fixation plates (such as the plates described above). The placement and attachment of the two separate plates are challenging due to time of application (due to placement of two plates vs. one), increased risk of tissue irritation, and complications caused by the plate screws. Those complications arise from the limited space for bone purchase and the fact that the two sets of screws converge at a 90 degree angle and make contact or otherwise interfere with each other. An alternative approach to strengthen the fixation is to use a thicker plate material (rather than using two plates), but the disadvantage of the thicker single plate is increased risk of soft tissue irritation.

There is a need in the art for an improved Lapidus fusion system and method.

BRIEF SUMMARY

Discussed herein are various bone deformity correction devices and methods.

In Example 1, a bone deformity correction device comprises an elongate body, an adjustable manipulation arm movably coupled to the elongate body, wherein the adjustable manipulation arm is configured to move axially and laterally, and a cutting guide removably attachable to the elongate body. The elongate body comprises a distal bone attachment structure and a proximal bone attachment structure.

Example 2 relates to the bone deformity correction device according to Example 1, further comprising an axial adjustment mechanism associated with the elongate body, wherein the adjustable manipulation arm is moveably coupled to the axial adjustment mechanism.

Example 3 relates to the bone deformity correction device according to Example 1, wherein the axial adjustment mechanism comprises a threaded axial adjustment rod rotatably coupled to the elongate body, and a coupling structure rotatably coupled to the threaded axial adjustment rod, wherein the adjustable manipulation arm is moveably coupled to the coupling structure.

Example 4 relates to the bone deformity correction device according to Example 3, wherein the adjustable manipulation arm comprises a threaded manipulation arm rod rotatably coupled to the coupling structure.

Example 5 relates to the bone deformity correction device according to Example 4, wherein the coupling structure comprises a first lumen configured to receive the threaded axial adjustment rod and a second lumen configured to receive the threaded manipulation arm rod.

Example 6 relates to the bone deformity correction device according to Example 5, wherein the first lumen has an axis that is transverse to an axis of the second lumen.

Example 7 relates to the bone deformity correction device according to Example 1, further comprising an elongate slot defined in the elongate body, wherein the cutting guide is slidably coupleable with the elongate body at the elongate slot.

Example 8 relates to the bone deformity correction device according to Example 1, wherein the cutting guide comprises a guide body comprising at least two saw blade slots defined therein, and a guide attachment body coupleable with the elongate body.

Example 9 relates to the bone deformity correction device according to Example 8, wherein the guide attachment body comprises at least two elongate slots defined within the guide attachment body.

Example 10 relates to the bone deformity correction device according to Example 9, further comprising at least two attachment bolts slidably coupled to the elongate body, wherein each of the at least two attachment bolts is slidably disposed within one of the at least two elongate slots.

In Example 11, a bone deformity correction system comprises a bone deformity correction device and a fixation plate. The bone deformity correction device comprises an elongate device body, an adjustable manipulation arm movably coupled to the elongate body, wherein the adjustable manipulation arm is configured to move axially and laterally, and a cutting guide removably attachable to the elongate device body. The fixation plate comprises four elongate structures coupled together to form a plate body, and at least two openings defined within the plate body.

Example 12 relates to the bone deformity correction system according to Example 11, wherein the elongate device body comprised a distal bone attachment structure, and a proximal bone attachment structure.

Example 13 relates to the bone deformity correction system according to Example 11, wherein the plate body comprises two extension structures extending from the plate body.

Example 14 relates to the bone deformity correction system according to Example 11, wherein a longitudinal axis of the adjustable manipulation arm is transverse to a longitudinal axis of the elongate device body.

In Example 15, a bone deformity correction device comprises an elongate body and an axial adjustment mechanism associated with the elongate body. The elongate body comprises a distal bone attachment structure and a proximal bone attachment structure, and the axial adjustment mechanism comprises a threaded axial adjustment rod rotatably coupled to the elongate body, and a coupling structure rotatably coupled to the threaded axial adjustment rod. The device further comprises an adjustable manipulation arm coupled to the coupling structure and a cutting guide removably attachable to the elongate body. The adjustable manipulation arm comprises a threaded manipulation arm rod rotatably coupled to the coupling structure and an extendable attachment structure rotatably couple to the threaded manipulation arm rod.

Example 16 relates to the bone deformity correction device according to Example 15, wherein a longitudinal axis of the adjustable manipulation arm is transverse to a longitudinal axis of the elongate body.

Example 17 relates to the bone deformity correction device according to Example 15, wherein the coupling structure comprises a first lumen configured to receive the threaded axial adjustment rod and a second lumen configured to receive the threaded manipulation arm rod.

Example 18 relates to the bone deformity correction device according to Example 17, wherein the first lumen has an axis that is transverse to an axis of the second lumen.

Example 19 relates to the bone deformity correction device according to Example 15, further comprising an elongate slot defined in the elongate body, wherein the cutting guide is slidably coupleable with the elongate body at the elongate slot.

Example 20 relates to the bone deformity correction device according to Example 15, wherein the cutting guide comprises a guide body comprising at least two saw blade slots defined therein, and a guide attachment body coupleable with the elongate body.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 10 is a perspective view of another step of the known procedure of FIG. 1A using known devices.

FIG. 2B is a top view of the bone deformity correction device of FIG. 2A, according to one embodiment.

DETAILED DESCRIPTION

The various embodiments herein relate to systems, devices, and methods for performing a bone deformity treatment procedure, which, according to certain embodiments, can be a Lapidus fusion procedure. In certain implementations, the system can be made up of a treatment device and a fixation plate. Alternatively, other embodiments relate to solely a treatment device, or solely a fixation plate.

Figure 1A:
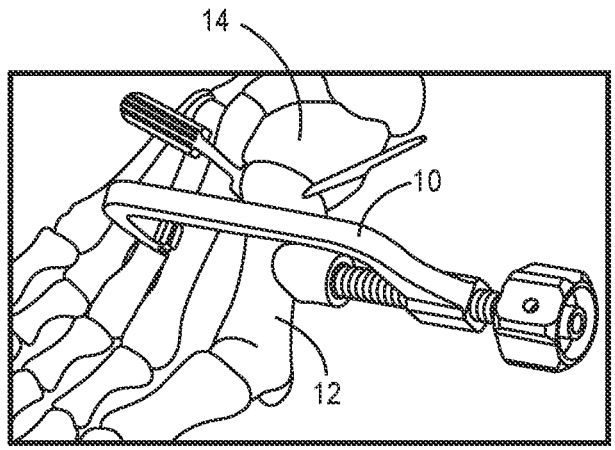
FIG. 1A is a perspective view of a step of a known procedure using known devices.
Figure 1B:
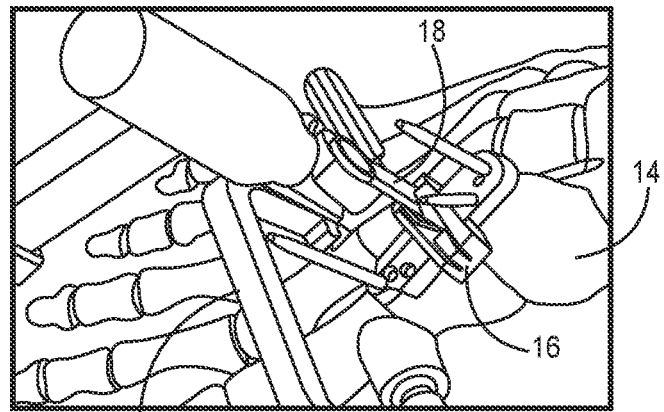
FIG. 1B is a perspective view of another step of the known procedure of FIG. 1A using known devices.
Figure 1C:
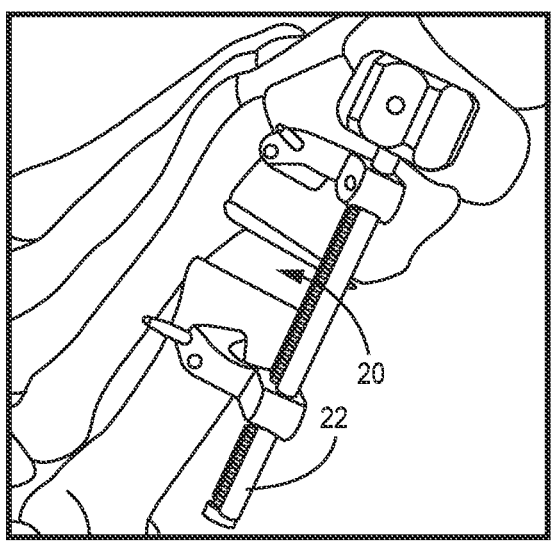
FIG. 1D is a perspective view of another step of the known procedure of FIG. 1A using known devices.
FIG. 1E is a perspective view of another step of the known procedure of FIG. 1A using known devices.
Figure 1D:
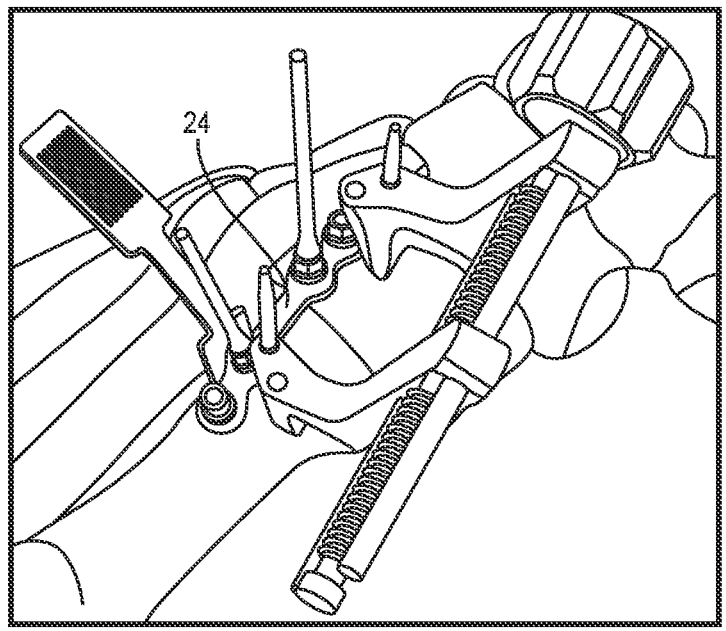
Figure 1E:
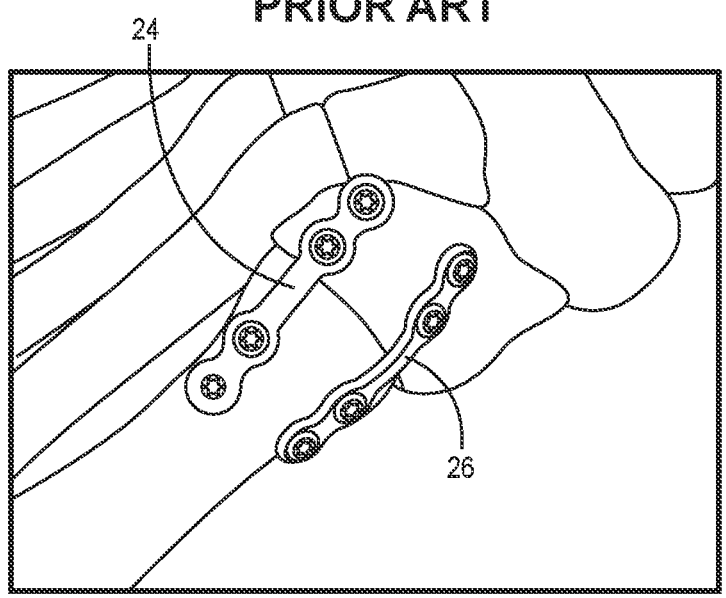
Figure 2A:
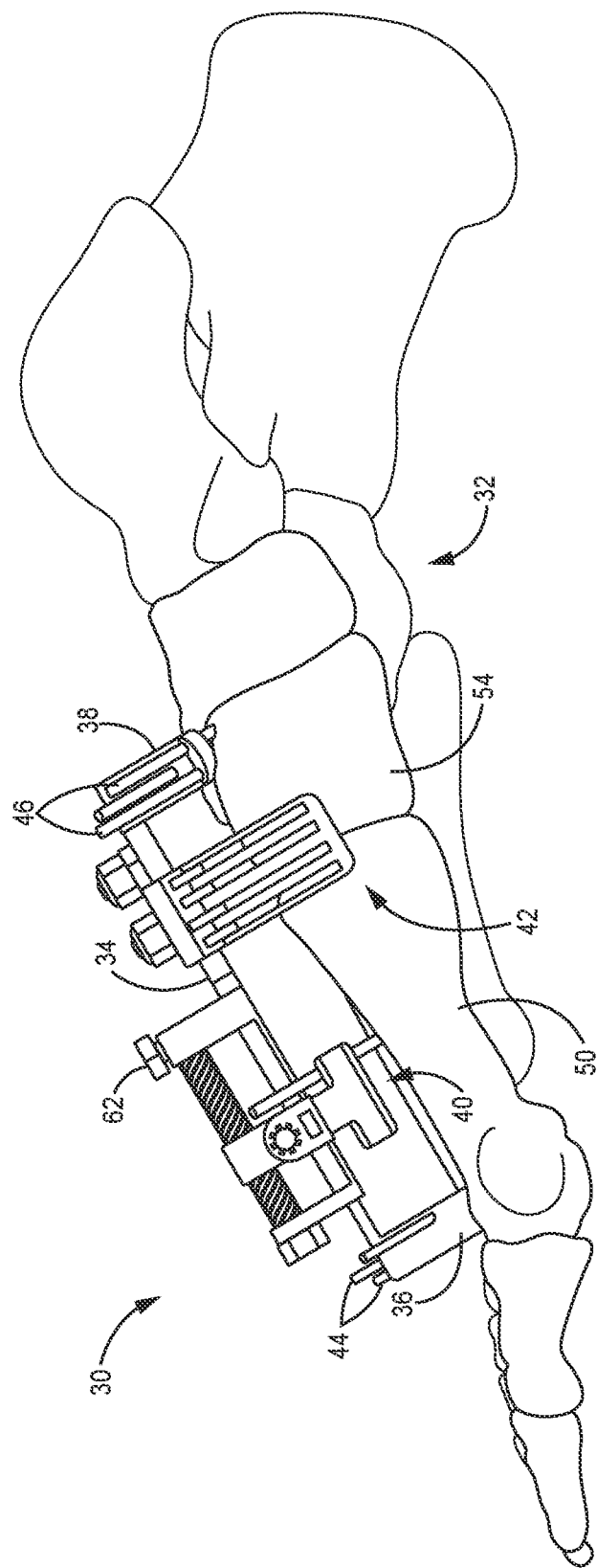
FIG. 2A is a side view of a bone deformity correction device attached to the foot bones of a patient, according to one embodiment.

One embodiment of the bone deformity treatment device 30 is depicted in FIGS. 2A-2B and FIGS. 3A-3D. FIGS. 2A and 2B depict the positioning of the device 30 on the foot 32 of a patient, while FIGS. 3A-3D depict various expanded views of the device 30. In this exemplary embodiment, the device 30 has an elongate body 34, a distal footing 36 at a distal end of the body 34, a proximal footing 38 at a proximal end of the body 34, a manipulation arm 40 slidably disposed on the elongate body 34, and a blade guide 42 adjustably disposed on the body 34. According to certain embodiments, the elongate body 34, the footings 36, 38, the manipulation arm 40, and the blade guide 42 can be made of an appropriate metal and/or plastic.

The distal footing 36 is a bone attachment structure 36 that is shaped to match and mate with the shape of a target bone (in this example, the second metatarsal 52) such that the distal footing 36 can be disposed on and attached to the bone as best shown in FIGS. 2B, 3B, 3C, and 3D. More specifically, the footing 36 is curved in a fashion that matches the curve of the bone (such as the second metatarsal 52). Alternatively, it is understood that the footing or attachment structure 36 can take any form or constitute any mechanism or component that allows for attachment to the target bone (such as the second metatarsal 52). Further, the footing 36 has at least two openings (not shown) defined therein that are configured to receive attachment pins 44 (which can, in certain implementations, be K-wires 44) such that the pins 44 can be positioned through the openings (not shown) and into the bone 52 to attach the footing 36 thereto. According to some embodiments, the at least two openings (not shown) are disposed at different angles to strengthen the attachment to the bone when the pins 44 are inserted therethough. In accordance with certain implementations, the openings (not shown) defined in the footing 36 in this embodiment are similar to the openings 237 discussed in detail below with respect to the device 230 embodiment of FIGS. 8A-8D. The attachment pins 44 and the other attachment pins discussed herein can be made of stainless steel or any other appropriate metal. In certain embodiments, as mentioned, any of the pins can be commercially available K-wires.

Similarly, the proximal footing 38 is a bone attachment structure 38 that is shaped to match and mate with the shape of another target bone (in this example, the medial cuneiform 54) such that the proximal footing 38 can be disposed on and attached to the bone as best shown in FIGS. 2B, 3A, 3B, and 3C. More specifically, the footing 38 is curved in a fashion that matches the curve of the bone (such as the medial cuneiform 54). Alternatively, it is understood that the footing or attachment structure 38 can take any form or constitute any mechanism or component that allows for attachment to the target bone (such as the medial cuneiform 54). Further, the footing 38 has at least two openings (not shown) defined therein that are configured to receive attachment pins 46 (which can, in certain implementations, be K-wires 46 or any commercially available olive wires) such that the pins 46 can be positioned through the openings (not shown) and into the bone 54 to attach the footing 38 thereto. According to some embodiments, the at least two openings (not shown) are disposed at different angles to strengthen the attachment to the bone when the pins 44 are inserted through the foot plate and into bone. In accordance with certain implementations, the openings (not shown) defined in the footing 38 in this embodiment are similar to the openings 239A, 239B discussed in detail below with respect to the device 230 embodiment of FIGS. 8A-8D.

In certain embodiments, the device 30 has an extendable arm 60 extendably attached to the elongate body 34 with the distal footing 36 disposed at the distal end of the arm 60. In the exemplary embodiment as shown, the extendable arm 60 is extendably and slidably disposed within an opening or lumen (not shown) defined along the length of the body 34. Further, a locking screw 62 is provided that is in communication with the extendable arm 60 such that the screw 62 can be rotated into contact with the arm 60, thereby creating frictional contact that is sufficient to lock the extendable arm 60 in place. Thus, the user (such as the surgeon) can use the locking screw 62 to release the extendable arm 60 or lock it in place 60, thereby allowing for adjustment of the position of the distal footing 36 in relation to the elongate body 34. As such, the user can use the extendable arm 60 to adjust the footing 36 based on the length of the patient's foot, thereby assuring that the footing 36 is positioned at the most desirable location along the length of the second metatarsal 52.

Figure 3A:
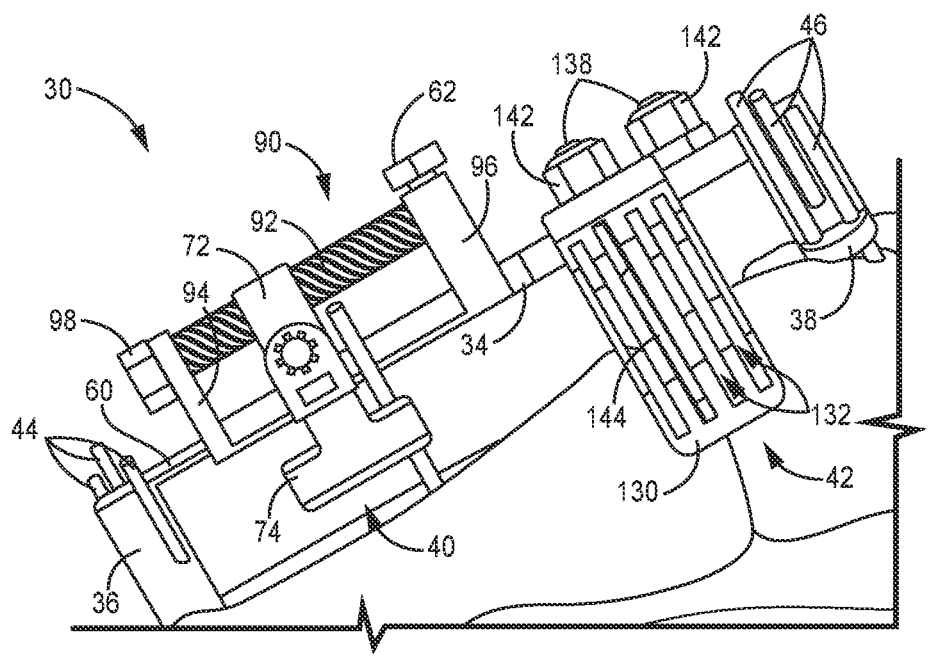
FIG. 3A is an expanded side view of the bone deformity correction device of FIG. 2A, according to one embodiment.
Figure 3B:
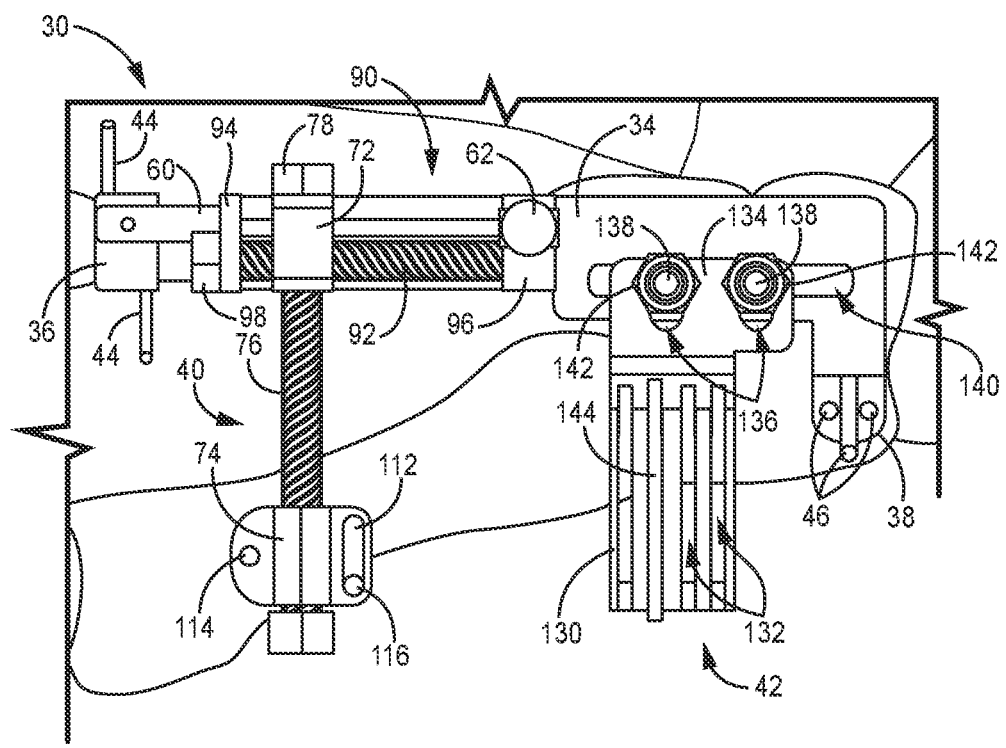
FIG. 3B is an expanded top view of the bone deformity correction device of FIG. 2A, according to one embodiment.
Figure 3C:
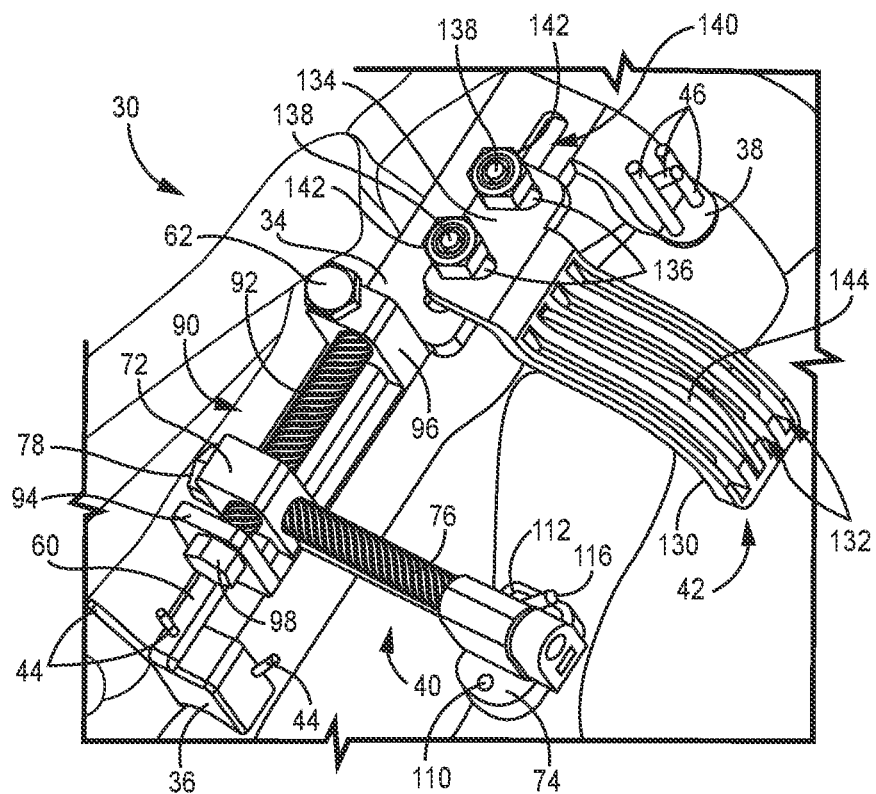
FIG. 3C is a perspective view of the bone deformity correction device of FIG. 2A, according to one embodiment.
Figure 3D:
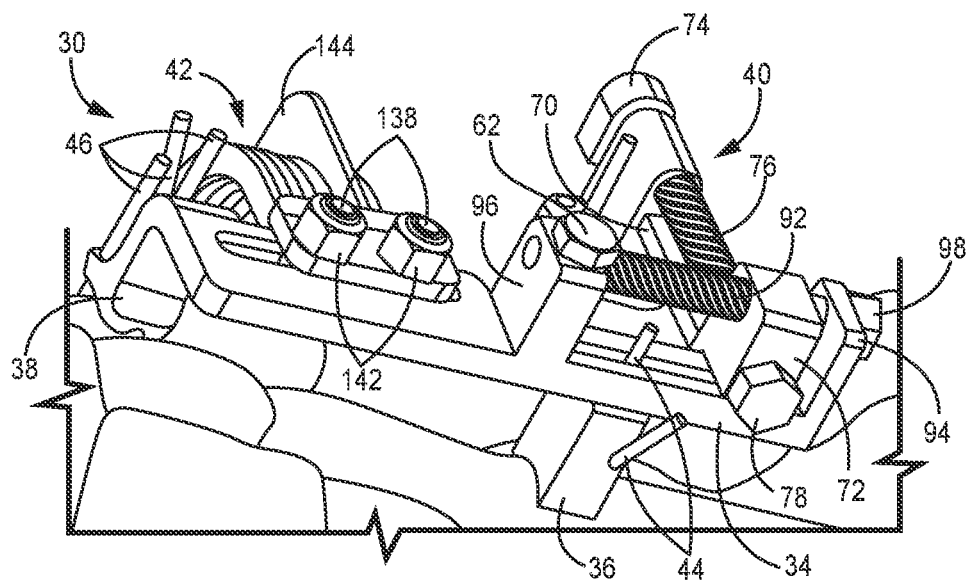
FIG. 3D is a perspective view of the lateral side of the bone deformity correction device of FIG. 2A, according to one embodiment.

In one implementation, the manipulation arm 40, as best shown in FIGS. 3C and 3D, is an adjustable length arm 40 that has a support arm 70 (as best shown in FIG. 3D) with an attachment block or coupling block (also referred to herein as a "coupling structure") 72 at the first end and an extendable footing (or "bone attachment structure") 74 slidably disposed at the second end. The manipulation arm 40 also has a rotatable threaded rod 76 that is disposed parallel to the support arm 70 and is rotatably disposed within the coupling structure 72 at the first end of the rod 76 and is rotatably disposed within the extendable footing 74 at the second end. At its first end, the rod 76 has a knob 78 such that the rod 76 extends through a first lumen (not shown) defined in the coupling structure 72 and a user can turn the knob 78 to turn the rotatable rod 76. The rod 76 is not threadably coupled to the attachment block 72 and thus can easily rotate in relation to the block 72. At its second end, the rod 76 is threadably coupled to the extendable footing 74 such that rotation of the rod 76 causes the footing 74 to be urged along the length of the rod 76. More specifically, the rod 76 is disposed within a lumen (not shown) defined within the footing 74 with matching threads defined within the lumen such that the threads on the rod 76 couple with the threads along the inner wall (not shown) of the lumen such that rotation of the rod 76 causes translation of the motion into axial movement of the footing 74 along the axis of the rod 76. Thus, a user can rotate the knob 78 to rotate the rod 76 in either direction and thereby cause the footing 74 to move toward or away from the elongate body 34 along the axis of the rod 76. The movement of the footing 74 is used to urge the bone to which the footing 74 is attached in the desired direction. For example, in those implementations in which the bone deformity is hallux valgus, the manipulation arm 40 can be referred to as the "intermetatarsal arm" 40 (and the rod 76 can be referred to as the "intermetatarsal rod" 76), and moving the footing 74 toward the elongate body 34 can result in the correction of the intermetatarsal angle by narrowing the angle between the first and second metatarsals, as will be discussed in further detail in the detailed description provided below of the exemplary use of the device embodiments herein.

In addition, according to this specific exemplary embodiment, the manipulation arm 40 is slidably disposed on the elongate body 34 via an axial adjustment mechanism 90. In this implementation, the axial adjustment mechanism 90 includes a threaded, rotatable rod 92 to which the manipulation arm 40 is attached such that rotation of the rod 92 causes movement of the manipulation arm 40 along the length of the elongate body 34. In this embodiment, the rod 92 is rotatably disposed at the first end through a lumen (not shown) defined in a first support 94 and is rotatably disposed at the second end through a lumen (not shown) defined in a second support 96 as shown. At its first end, the rod 92 has a knob 98 such that a user can turn the knob 98 to turn the rotatable rod 92. The rod 92 is not threadably coupled to the first support 94 or the second support 96 and thus can easily rotate within the lumens (not shown) in relation to both supports 94, 96.

The manipulation arm 40 is coupled to the axial adjustment mechanism 90 via the coupling structure 72. That is, the coupling structure 72 has a second lumen (not shown) defined therein that is transverse to its first lumen (not shown). More specifically, the second lumen has an axis that is parallel to (and concentric with) the axis of the rotatable rod 92, while the first lumen (not shown) has an axis that is transverse to the second lumen and is parallel to (and concentric with) the axis of the rotatable rod 76 of the manipulation arm 40. The rotatable rod 92 of the axial adjustment mechanism 90 is rotatably disposed through the second lumen (not shown). Further, the external threads on the rod 92 are mateable with threads (not shown) defined in the inner surface of the second lumen (not shown) such that rotation of the rod 92 causes movement of the attachment block 72 along the axis of the rod 92 (and thereby along the length of the elongate body 34). In accordance with certain implementations, the first and second lumens (not shown) defined in the structure 72 in this embodiment are similar to the first and second lumens 273, 275 discussed in detail below with respect to the device 230 embodiment of FIGS. 8A-8D. Thus, rotation of the knob 98 by a user (such as a surgeon) causes the rod 92 to rotate, thereby causing the attachment block 72 to move along the length of the rod 92. Rotation of the rod 92 in one direction causes the block 72 to move in one direction along the rod 92, while rotation of the rod 92 in the other direction causes the block 72 to move in the other direction along the rod 92. The movement of the block 72 is used to urge the bone to which the footing 74 is attached in the desired direction. For example, in those implementations in which the bone deformity is hallux valgus, the axial adjustment mechanism 90 can be referred to as the "compression-distraction mechanism" 90 (and the rod 92 can be referred to as the "compression-distraction rod" 92), and moving the footing 74 in one direction can result in distraction of the first metatarsal, while moving the footing 74 in the other direction can result in compression of the first metatarsal, as will be discussed in further detail in the detailed description provided below of the exemplary use of the device embodiments herein.

Alternatively, one of ordinary skill in the art would understand that the axial adjustment mechanism 90 can be any known mechanism or have any known configuration and can have any known components/features that provide for moving the manipulation arm 40 axially along the length of the rod 92 and further that the manipulation arm 40 can be any known mechanism or have any known configuration and can have any known components/features that provide for urging the footing 74 toward or away from the elongate body 34.

According to one embodiment, the extendable footing 74 of the manipulation arm 40 is an bone attachment structure 74 that can be disposed on (or above) and attached to the target bone (which, in this example, is the first metatarsal 50) as best shown in FIGS. 3A-3C, for example. In one specific implementation as shown, the underside of the footing 74 is flat and may not contact the target bone (such as the first metatarsal 50), as best shown in FIG. 3A. Alternatively, the footing 74 can be curved in a fashion that matches the curve of the bone (such as the first metatarsal 50). Alternatively, it is understood that the footing or attachment structure 74 can take any form or constitute any mechanism or component that allows for attachment to the target bone. Further, the footing 74 has a fixed opening 110 and a slot opening 112 as best shown in FIG. 3C. As best shown in FIG. 3B, the fixed opening 110 is sized and configured to receive a fixation pin 114 such that the pin 114 cannot be urged in any direction transverse to the longitudinal axis of the pin 114. In contrast, the slot opening 112 has a length that is parallel to the longitudinal axis of the manipulation arm 40. As such, as also shown in FIG. 3B, the slot 112 is sized and configured to receive a fixation pin 116 such that the pin 116, while disposed within the slot 112, can be urged in a direction transverse to the longitudinal axis of the pin 116 (and parallel to the longitudinal axis of the arm 40). As such, the pins 114, 116 can be positioned through the openings 110, 112 and into the bone 50 to attach the footing 74 thereto, while also allowing movement of pin 116 within the slot 112. As discussed elsewhere, the attachment pins 114, 116, like any of the attachment pins discussed elsewhere herein, can be made of stainless steel or any other appropriate metal. In certain embodiments, as mentioned, any of the pins can be commercially available K-wires. The rotation of the pin 116 can urge the bone to which the pin 116 is attached to rotate in the desired direction. For example, in those implementations in which the bone deformity is hallux valgus, rotating the pin 116 can result in rotation of the first metatarsal in the frontal plane as desired, as will be discussed in further detail in the detailed description provided below of the exemplary use of the device embodiments herein.

As mentioned above, the device 30 also has an adjustable bone saw blade guide 42 that is removably attachable to the body 34 as best shown in FIGS. 3A, 3B, and 3C. The guide 42 has a guide body 130 with two or more slots 132 defined therein, wherein each of the slots 132 can receive and guide a saw blade for use in resection of a target bone (as will be discussed in further detail below). The guide 42 also has an attachment body 134 attached to the guide body 130 that has at least two elongate openings 136 defined therein that can receive at least two lockable bolts 138 that can be disposed therethrough. Further, the elongate body 34 has a slot 140 defined therein that can receive the lockable bolts 138 as well, such that the bolts 138 are disposed through the guide openings 136 and the slot 140. Each of the lockable bolts 138 have a lockable nut 142 rotatably attached thereto such that the nuts 142 can be used to either loosen the bolts 138 or lock them in place. Thus, rotation of the nuts 142 in one direction can loosen the bolts 138 and thereby loosen the guide attachment body 134 such that the guide 42 can be moved axially along the length of the slot 140 or transversely along the length of the elongate openings 136, thereby allowing for positioning the guide 42 in relation to the target bones 50, 54 for resection as will be discussed in further detail below. Alternatively, the guide 42 can be adjustably coupled to the body 34 via any known mechanism or configuration and can have any known components/features that provide for adjustable and removable coupling to the body 34.

In certain implementations, the guide 42 can also have a slot key 144 that is slidable into each of the guide slots 132 such that the key 144 can be used to help adjust the position of the device 30 and/or the guide 42 to match the shape of the target bones 50, 54.

In use, the device 30 can be used in the following fashion to perform a procedure to treat a bone deformity, as best shown in FIGS. 4A-5C. In this specific example, the exemplary bone deformity is hallux valgus, but it is understood that the device 30 can be used to treat many different types of bone deformities in various bones of the human body, as also discussed elsewhere herein. It is also understood that there are various incisions to be made as part of this procedure (and any other relevant procedure), but the description herein will focus on the device 30, the attachment of the device 30 to the target foot, and the interaction with the device 30 and the foot.

Figure 4A:
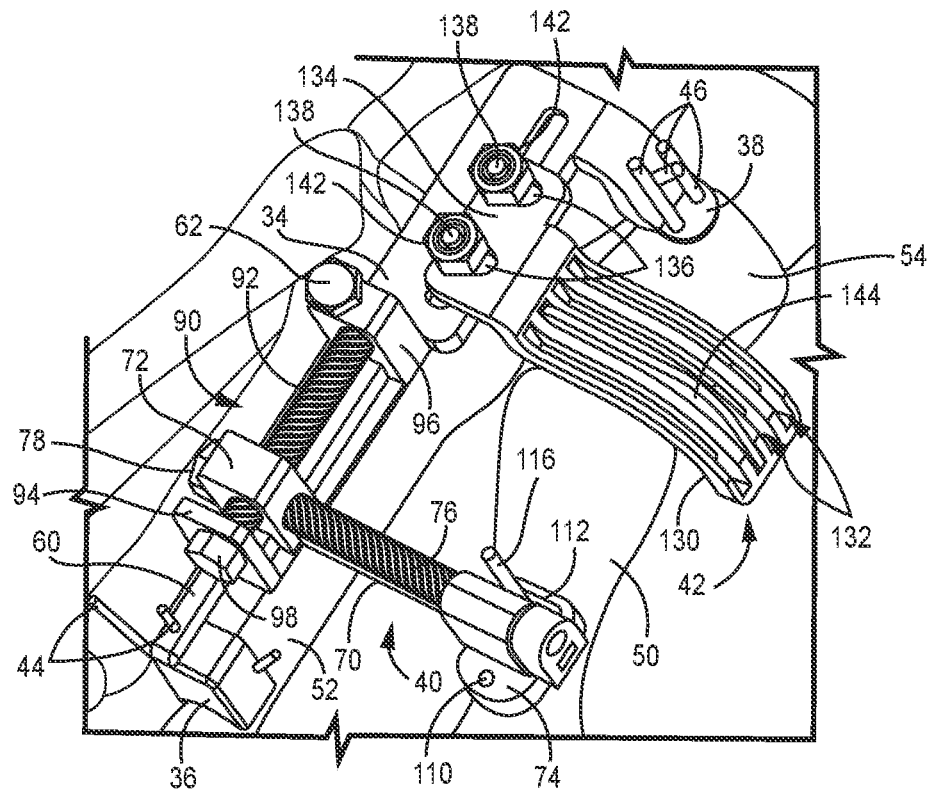
FIG. 4A is a perspective view of the bone deformity correction device of FIG. 2A with a fixation pin 116 attached to the target bone through the slot 112, according to one embodiment.

As best shown in FIG. 4A, according to one embodiment, in the hallux valgus example, the device 30 is positioned on the foot, and the proximal footing 38 is positioned on and attached to the medial cuneiform 54. More specifically, one attachment pin 46 is disposed through at least one opening defined in the footing 38 and into the bone 54.

Once the proximal footing 38 is attached via one attachment pin 46 to the medial cuneiform 54, the distal footing 36 is then positioned as desired on the second metatarsal 52. In those device embodiments with an extendable arm (such as the device 30 with the extendable arm 60 as described above, the location of the footing 36 can be adjusted based on the length of the second metatarsal 52 using the extendable arm 60. That is, the locking screw 62 is loosened such that the extendable arm 60 can be moved, and the arm 60 is moved in relation to the elongate body 34 such that the footing 36 is disposed at the desired location along the length of the second metatarsal 52. Once the footing 36 is in the desired position, the locking screw 62 is tightened, thereby locking the extendable arm 60 in place.

At this point, whether the specific device embodiment has an extendable arm or not, the user then attaches the distal footing 36 to the second metatarsal 52 at the desired location. More specifically, an attachment pin 44 is disposed through an opening (not shown) defined in the footing 36 and into the bone 52. According to certain embodiments, imaging can be used to confirm that the device 30 is positioned on the patient's foot such that the elongate body 34 is substantially parallel to the second metatarsal 52. Once the desired positioning of the device 30 is confirmed, the footings 36, 38 can be more securely attached to the bones 52, 54. That is, additional attachment pins 44, 46 are positioned through the openings in the footings 36, 38 and into the bones 52, 54, thereby stabilizing the device 30 to the bones 50, 52.

Alternatively, the distal footing 36 is attached to the second metatarsal 52 first, and then the proximal footing 38 is attached to the medial cuneiform 54.

At this point, the position of the manipulation arm 40 along the length of the elongate body 34 is adjusted using the axial adjustment mechanism 90 such that the manipulation arm 40 is disposed at the appropriate position along the length of the first metatarsal 50. More specifically, the knob 98 is turned by the user to rotate the rotatable rod 92, thereby urging the arm 40 in one direction or the other (depending on the direction of the rotation of the knob 98) via the attachment block 72 through which the rotatable rod 92 is disposed. When the arm 40 is positioned such that the extendable footing 74 is disposed at the appropriate location along the length of the first metatarsal 50, an attachment pin 116 is disposed through the slot opening 112 and into the bone 50.

Figure 4B:
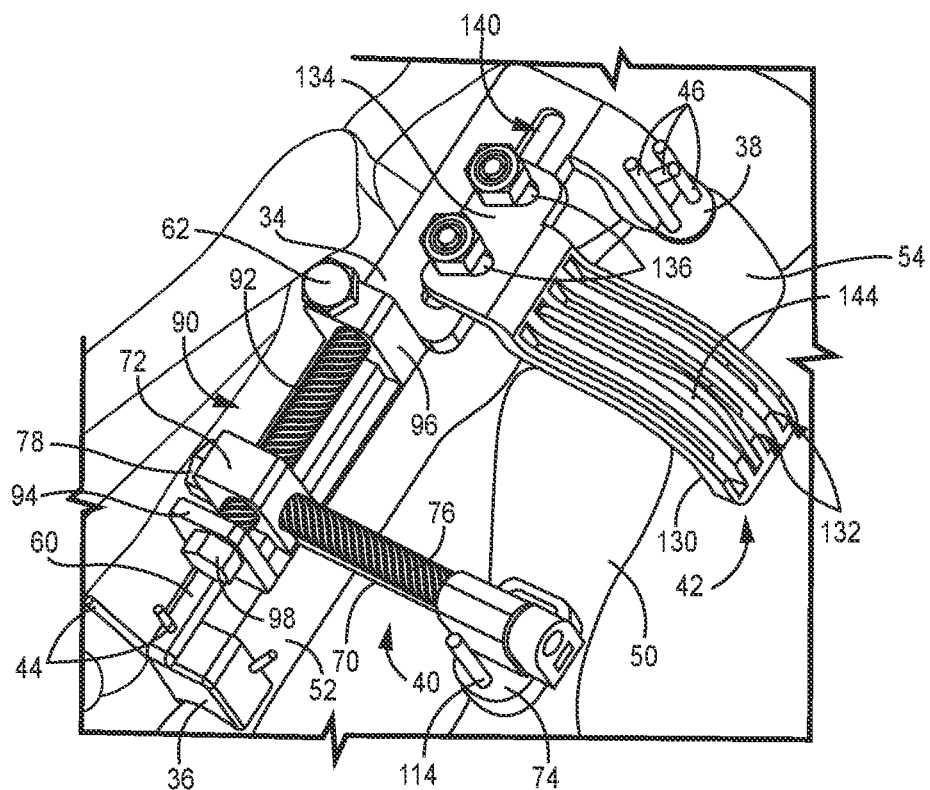
FIG. 4B is a perspective view of the bone deformity correction device of FIG. 2A with a fixation pin 114 attached to the target bone through the opening 110, according to one embodiment.

Once the attachment pin 116 is positioned into the bone 50, the pin 116 is then rotated in the lateral direction as shown in FIG. 4A, thereby causing rotation of the bone 50 in the lateral direction (and thus helping to correct the frontal plane deformity of the bone 50). In certain implementations, the correction can be assessed using imaging. Once it is confirmed that the bone 50 is positioned as desired, the attachment pin 114 is inserted through the fixed opening 110 and into the bone 50 as best shown in FIG. 4B, thereby capturing and securing the rotational alignment of the bone 50.

Figure 4C:
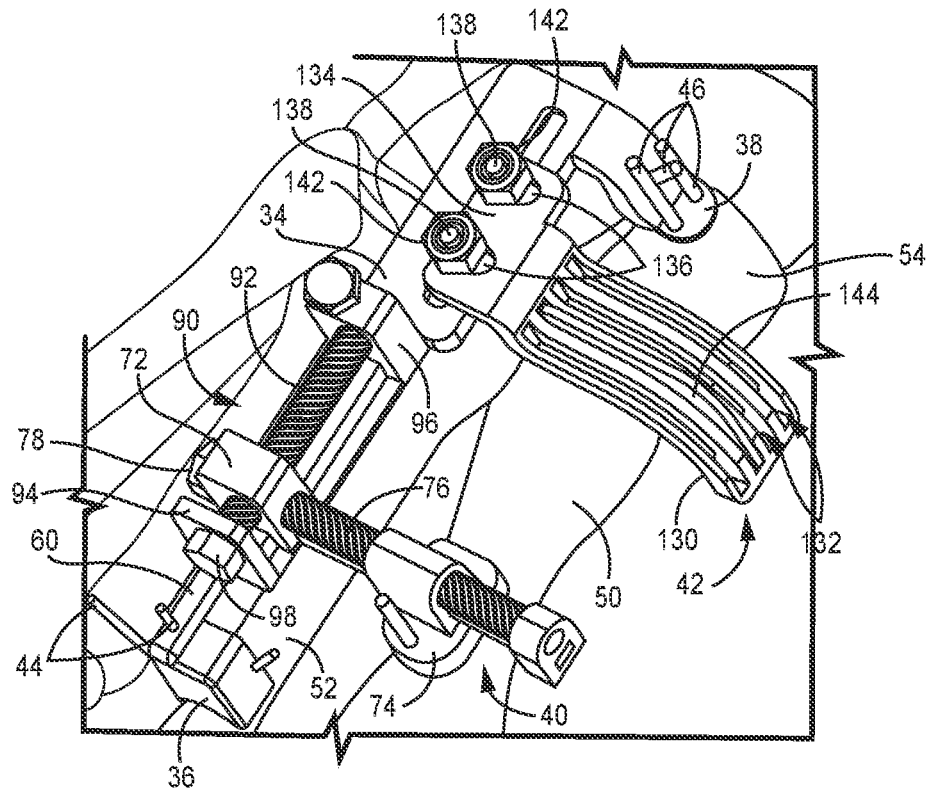
FIG. 4C is a perspective view of the bone deformity correction device of FIG. 2A in which the footing 74 has been urged toward the elongate body 34, according to one embodiment.

Once the bone 50 is rotationally aligned as desired, the next step is to address the deformed inter-metatarsal angle (the disposition of the first metatarsal 50 in relation to the second metatarsal 52). More specifically, the adjustable length of the manipulation arm 40 is used to urge the first metatarsal bone 50 into the desired, corrected position. The user rotates the knob 78 to cause the rotation of the rotatable rod 76, thereby urging the extendable footing 74 in the lateral direction, which urges the first metatarsal 50 in the lateral direction, as best shown in FIG. 4C (in which the footing 74 has been urged closer to the attachment block 72). This continues until the inter-metatarsal angle is adjusted as desired such that the first metatarsal 50 is positioned in its non-deformed position. At this point, any additional attachment pins can be inserted into additional fixed openings in the footing 74 and into the bone 50, thereby further securing it in place.

Next, the guide 42 will be used to resect a portion of both the first metatarsal 50 and a portion of the medial cuneiform 54. First, the position of the guide 42 is adjusted to ensure that it is positioned as desired in relation to the bones 50, 54. That is, the nuts 142 are loosened in relation to the bolts 138, thereby loosening the guide 42 in relation to the elongate body 34. Once the guide 42 is loosened, the guide 42 can be positioned as desired in relation to the bones 50, 54 to ensure the desired resection. That is, the guide 42 is positioned to allow a desired amount and angle of bone to be resected from the medial cuneiform 54. When repositioned as desired, the guide 42 is secured in place by tightening the nuts 142 and thereby tightening the bolts 138 and fixing the guide 42 in place. Further, in certain implementations, the desired positioning of the guide 42 can be confirmed with imaging.

Further, in conjunction with the positioning of the guide 42, the target resection site on the bone 54 is distracted. That is, the knob 98 is turned by the user (such as the surgeon) to cause the rotatable rod 92 to rotate such that the manipulation arm 40 is urged distally (away from the medial cuneiform 54), thereby urging the first metatarsal 50 away from the medial cuneiform 54.

Figure 5A:
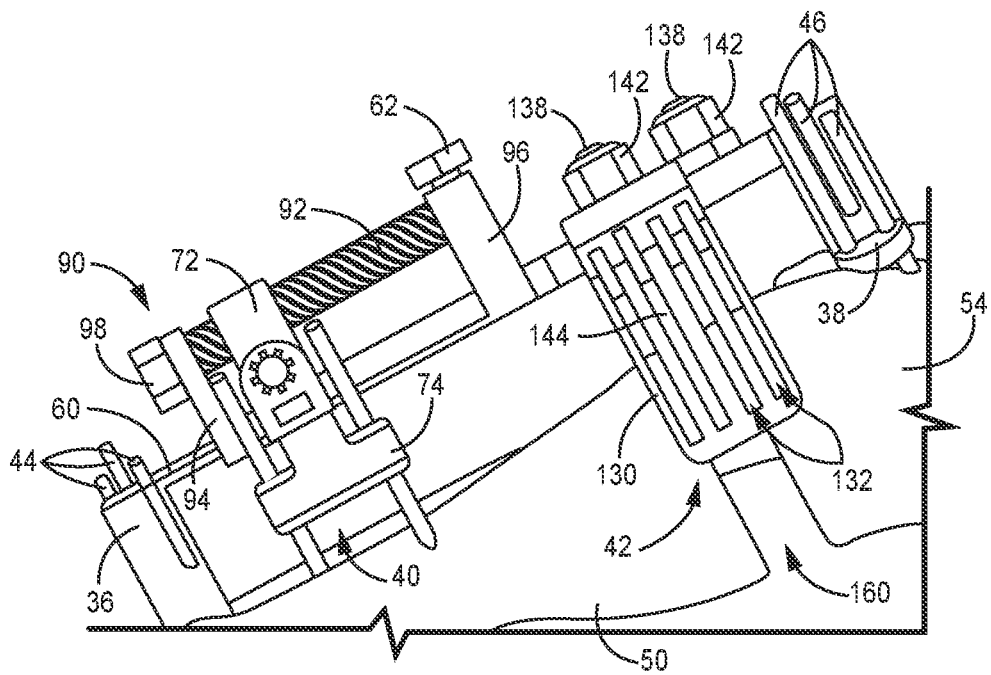
FIG. 5A is a side view of the bone deformity correction device of FIG. 2A after the first metatarsal and the medial cuneiform have been cut with a bone saw, according to one embodiment.
Figure 5B:
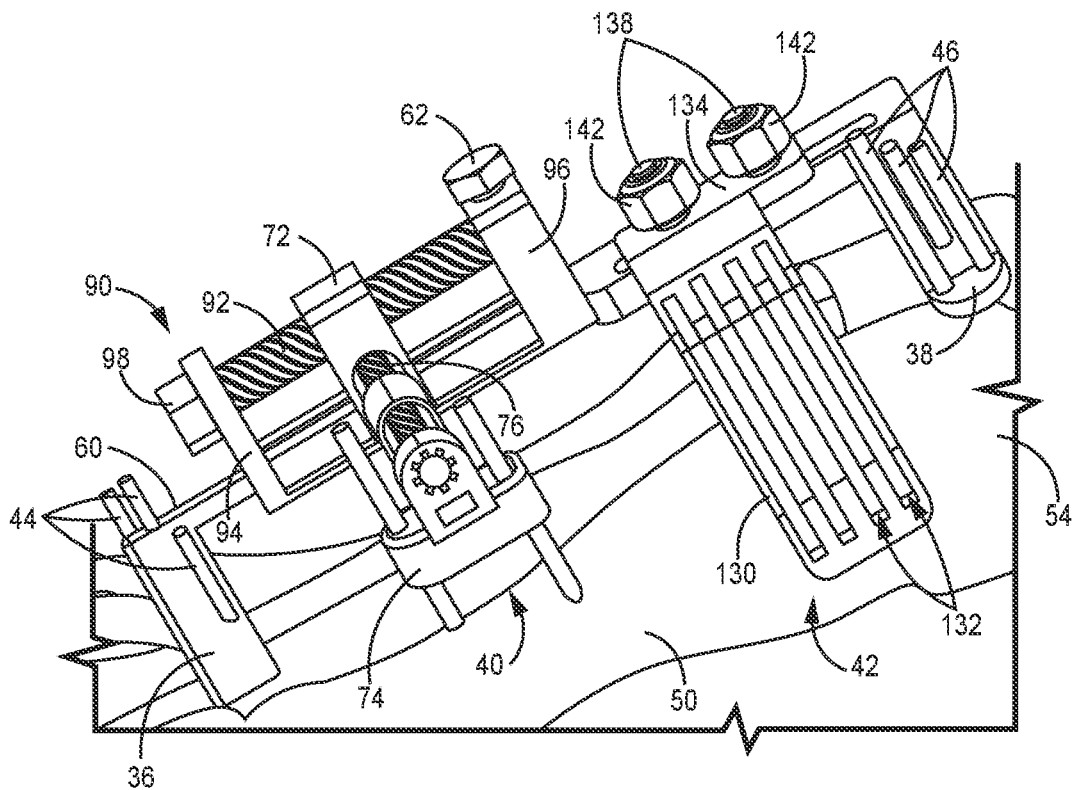
FIG. 5B is a side view of the bone deformity correction device of FIG. 2A after the first metatarsal has been urged proximally into contact with the medial cuneiform, according to one embodiment.

Once the guide 42 is positioned as desired and the first metatarsal 50 has been urged distally, the resection is performed. More specifically, a saw is first inserted through the desired slots 132 in the guide 42 to resect a portion of the medial cuneiform 54. In one embodiment, the portion resected is a distal portion of the medial cuneiform 54. The slot key 144 is then placed through a slot 132 and into the medial cuneiform 54 cut to stabilize the guide 42. Once the slot key 144 is positioned as desired, the knob 98 is turned to position the guide 42 such that a slot 132 of the guide is disposed at the appropriate location in relation to the first metatarsal 50. Alternatively, in certain implementations, the guide 42 may not need to be repositioned, because one of the slots 132 may already be positioned to allow for the desired resection of the first metatarsal 50 without having to move the guide 42. When positioned appropriately, the saw is again inserted through the guide 42 (via the appropriate slot 132) to resect a proximal portion of the first metatarsal 50. These two cuts create a gap 160 between the first metatarsal 50 and the medial cuneiform 54 as shown in FIG. 5A.

Figure 5C:
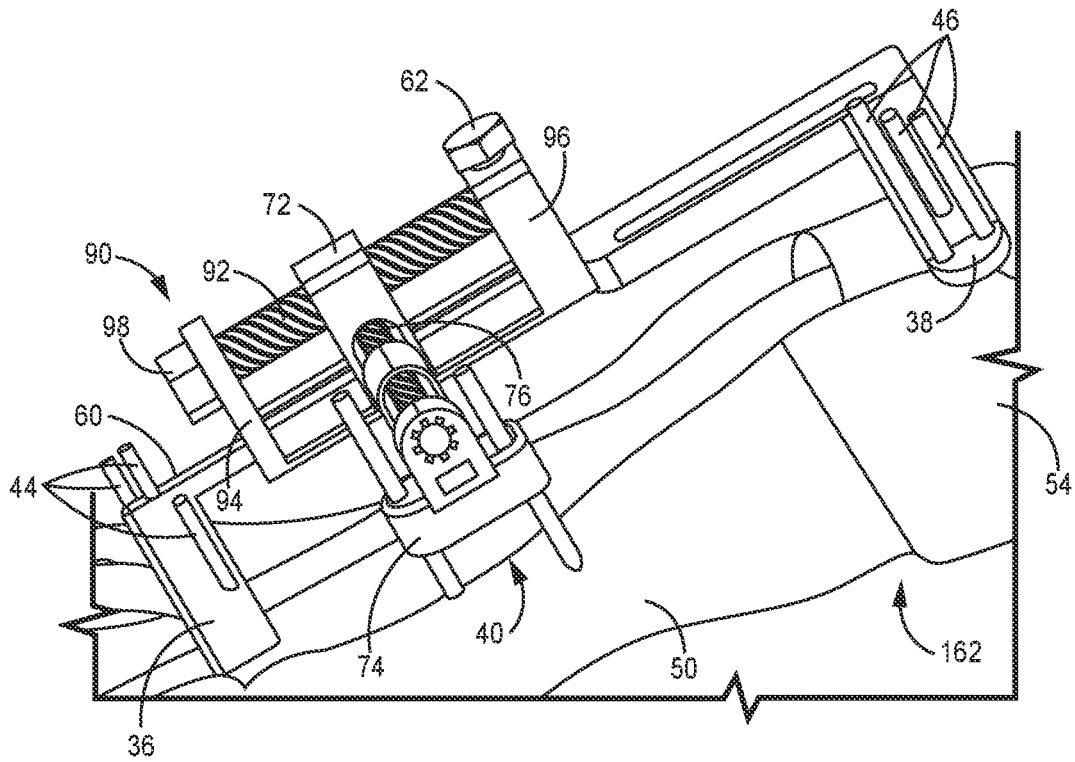
FIG. 5C is a side view of the bone deformity correction device of FIG. 2A with the bone saw guide body removed, according to one embodiment.

Once the gap 160 is formed, the guide 42 is removed from the elongate body 34, as best shown in FIG. 5C. Once the guide 42 is removed, the axial adjustment mechanism 90 is used to urge the first metatarsal 50 toward the medial cuneiform 54. More specifically, the knob 98 is turned to cause the rod 92 to rotate, thereby urging the manipulation arm 40 proximally, which urges the first metatarsal 50 proximally toward the medial cuneiform 54. Ultimately, this movement of the first metatarsal 50 causes the proximal end of the first metatarsal 50 into contact with the resected portion of the medial cuneiform 54 to form the fusion site 162, as shown in FIG. 5C. Increased compression between the two bones is achieved with each additional turn of the knob 98. At this point, imaging can be used to confirm the successful formation of the fusion site 162 and thus the multiplanar correction.

Figure 6A:
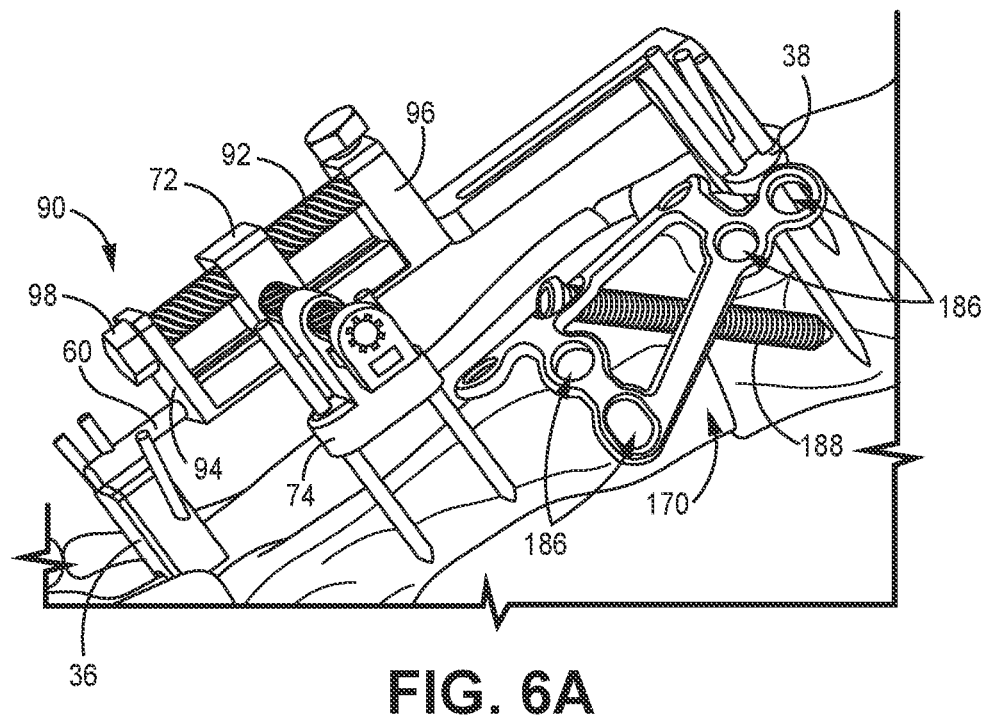
FIG. 6A is a side view of the bone deformity correction device of FIG. 2A with a fixation plate attached to the bone at the fusion site, according to one embodiment.

In accordance with certain embodiments as best shown in FIGS. 6A-7C, the system described herein can also include a fixation plate 170. Alternatively, the fixation plate 170 embodiments as disclosed herein can also be used independently of the deformity treatment device 30. As best shown in FIG. 7A, one implementation of the fixation plate 170 has a plate body 172 with four sides (or struts) 174, 176, 178, 180 and two projections 182, 184 extending therefrom. In addition, as best shown in FIG. 6A, the plate 170 has multiple openings 186 extending therethrough such that attachment screws 188 (as shown in FIGS. 6A-7C) can be inserted therethrough and into the target bone. In the various fixation plate 170 embodiments disclosed or contemplated herein, the body 172 and screws 188 can be made of either stainless steel or titanium. Alternatively, the body 172 and screws 188 can be made of any metal having similar characteristics to stainless steel and titanium.

Figure 6B:
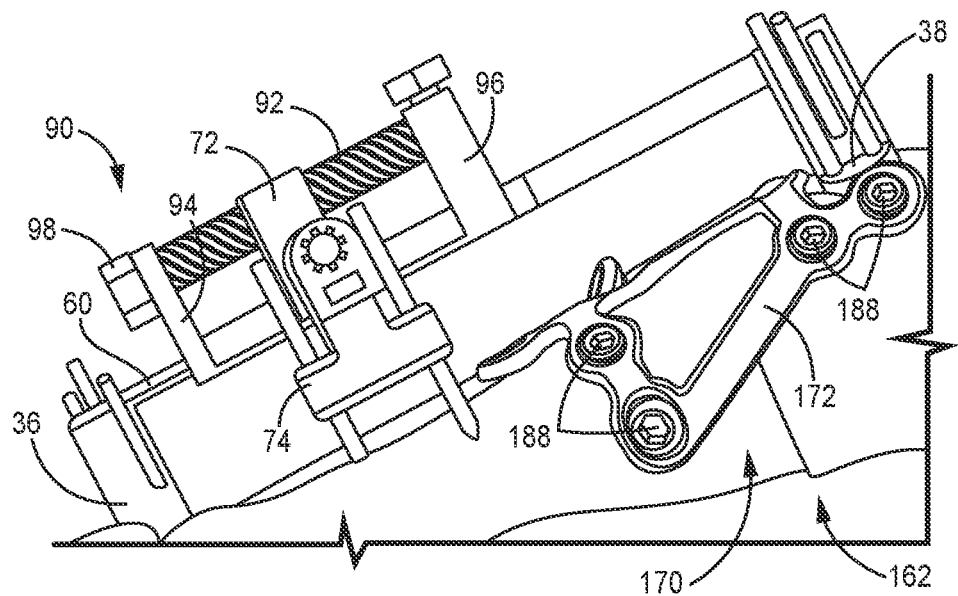
FIG. 6B is a side view of the bone deformity correction device of FIG. 2A with the fixation plate attached to the bone at the fusion site, according to one embodiment.
Figure 7A:
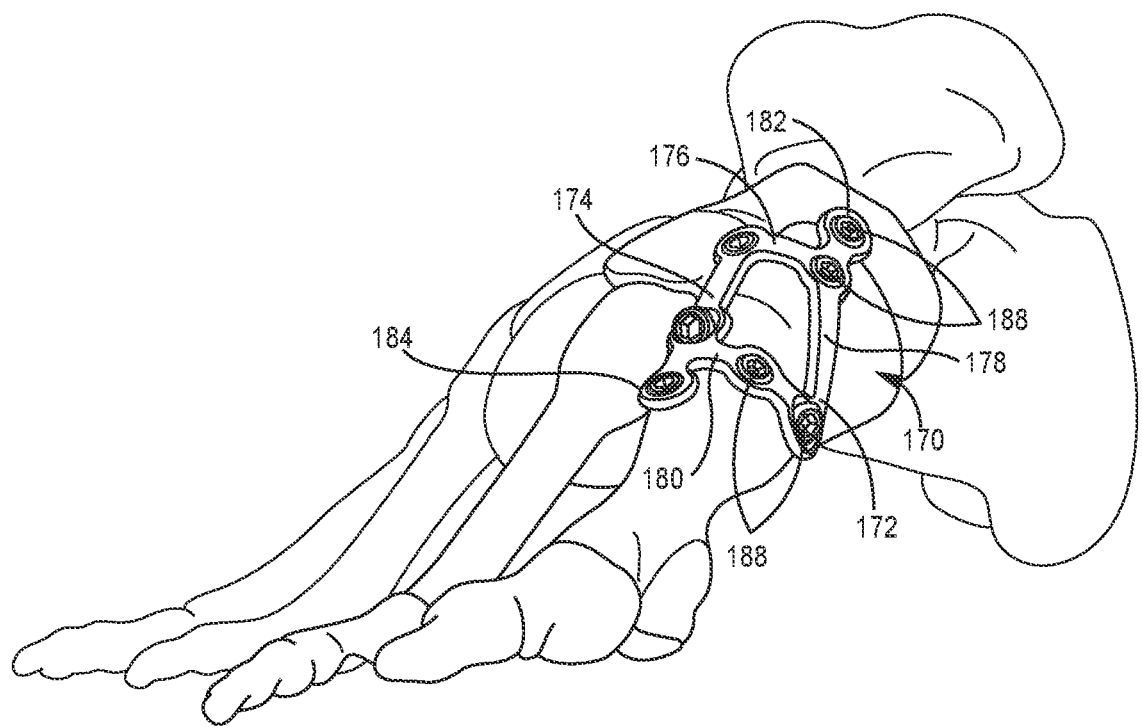
FIG. 7A is a perspective view of the fixation plate after the bone deformity correction device has been removed, according to one embodiment.
Figure 7B:
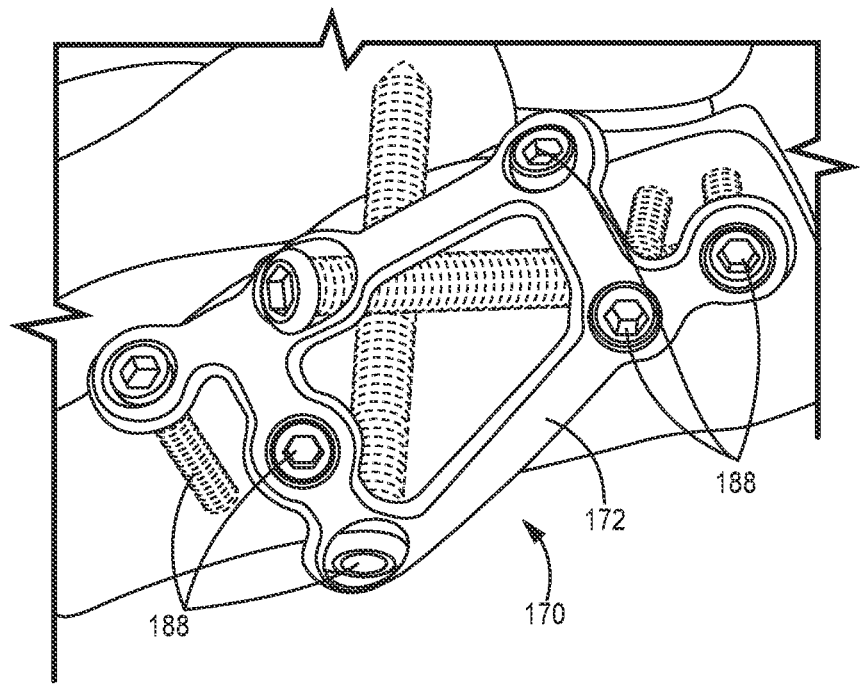
FIG. 7B is a top view of the fixation plate of FIG. 7A, according to one embodiment.
Figure 7C:
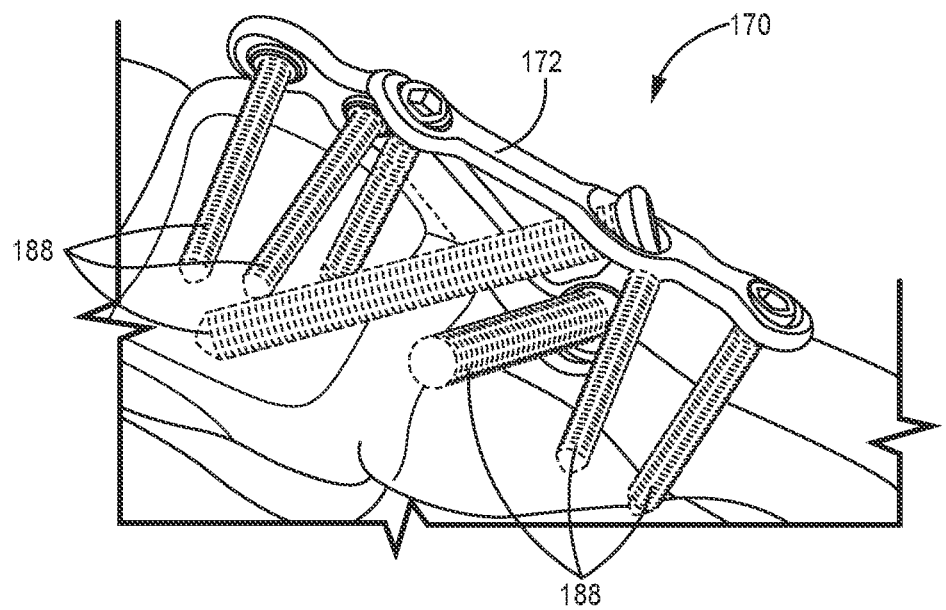
FIG. 7C is a side view of the fixation plate of FIG. 7A, according to one embodiment.

As best shown in FIGS. 6A and 6B, when used in conjunction with the device 30 as described above or any other similar device or system, the fixation plate 170 can be attached to the fusion site (such as fusion site 162) to fix the first metatarsal 50 and the medial cuneiform 54 in place at the fusion site 162. More specifically, once the procedure is performed (such as the procedure described above with respect to the device 30, the fixation plate 170 can be used to secure the fusion site 162 by positioning the plate body 172 across the fusion site 162 and inserting the attachment screws 188 through the openings 186 and into the bones 50, 54, with some of the screws 188 being inserted into the first metatarsal 50 and some of the screws 188 being inserted into the medial cuneiform 54 in this specific example. Once the fixation plate 170 is fixed in place and thereby securing the fusion site 162, the device 30 can be removed.

In this exemplary embodiment, the plate body 172 is shaped and configured such that the fixation plate 170 can be positioned on and attached to the bones 50, 54 without first removing the device 30. That is, the shape of the body 172 allows positioning of the body 172 at the fusion site 162 without interfering with or contacting any portion of the device 30. Further, the biplanar design of the plate 170 allows for use of thinner metal material in the body 172 without sacrificing strength of the plate 170. In addition, the configuration of the body 172 and the positioning of the openings 186 thereon allow for the screws 188 to be positioned therethrough without interference occurring between the screws 188. In contrast, two separate known plates as described in the Background typically have problems with such interference.

Separately, in accordance with certain embodiments, the configuration of the device 30 allows for positioning the fixation plate 170 or any other known fixation plate at the fusion site 162 without having to first remove the device 30. That is, as best shown in FIGS. 5A and 5C, the device 30 provides sufficient "clearance" or distance between the elongate body 34 and the target bones below at the fusion site 162 such that a variety of known fixation plate designs can be positioned at the fusion site 162 without being hindered or blocked in any fashion by the device 30. As such, many known fixation plate or the above plate 170 can be used in conjunction with any device embodiment herein by first removing the guide (such as guide 42) and then taking advantage of the clearance between the target bones and the device body (such as body 34) to position the fixation plate over the fusion site 162 and attach it thereto. According to certain alternative implementations, in addition to, or instead of, the fixation plate (such as plate 170 or any other known plate), a known interfragmentary lag screw (not shown) or other known fixation device can be used. With respect to the lag screw, it can be oriented dorsally from the first metatarsal to the plantar aspect of the medial cuneiform, or alternatively from the medial cuneiform dorsally to the plantar aspect of the first metatarsal.

Alternatively, as mentioned above, the fixation plate 170 can be used with any deformity treatment device or independently of any deformity treatment devices to fix two bones together for treatment purposes.

Another embodiment of a bone deformity treatment device 230 is depicted in FIGS. 8A-8D. In this exemplary implementation, the device 230 has an elongate body 234, a distal footing 236 at a distal end of the body 234, a proximal footing 238 at a proximal end of the body 234, a manipulation arm 240 slidably disposed on the elongate body 234, and a blade guide 242 adjustably disposed on the body 234. Each of these components and the additional features and components therein are substantially similar to and have substantially the same functions and characteristics as the corresponding components and features in the device 30 embodiment described above and depicted in FIGS. 2A-6B, except as described in further detail below.

In one implementation, the distal bone attachment structure 236 has three openings 237 defined therein that are configured to receive attachment pins (such as pins 44 described above) such that the pins can be positioned through the openings 237 and into the target bone (such as bone 52 as discussed above) to attach the footing 236 thereto. The three openings 237 are disposed at different angles to strengthen the attachment to the target bone when the pins are inserted therethrough. Alternatively, the footing 236 can have one, two, four, or any other number of openings.

Figure 8A:
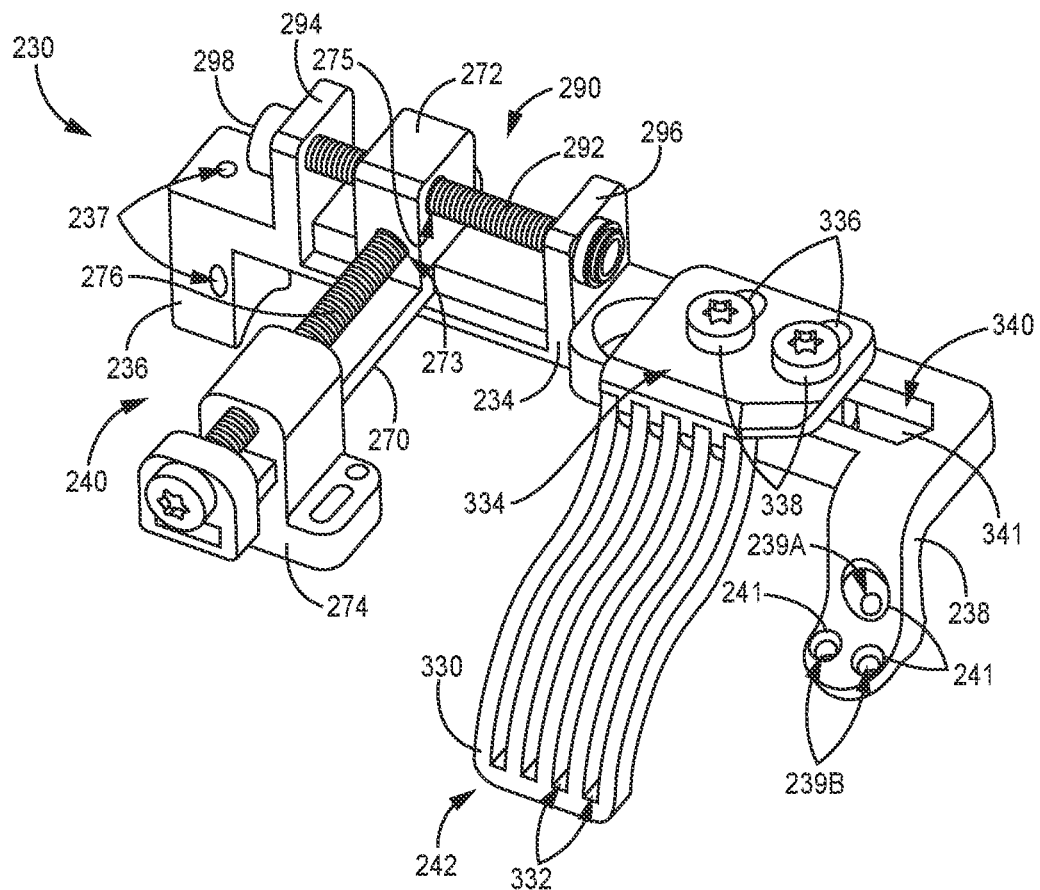
FIG. 8A is a perspective view of a bone deformity correction device, according to another embodiment.
Figure 8B:
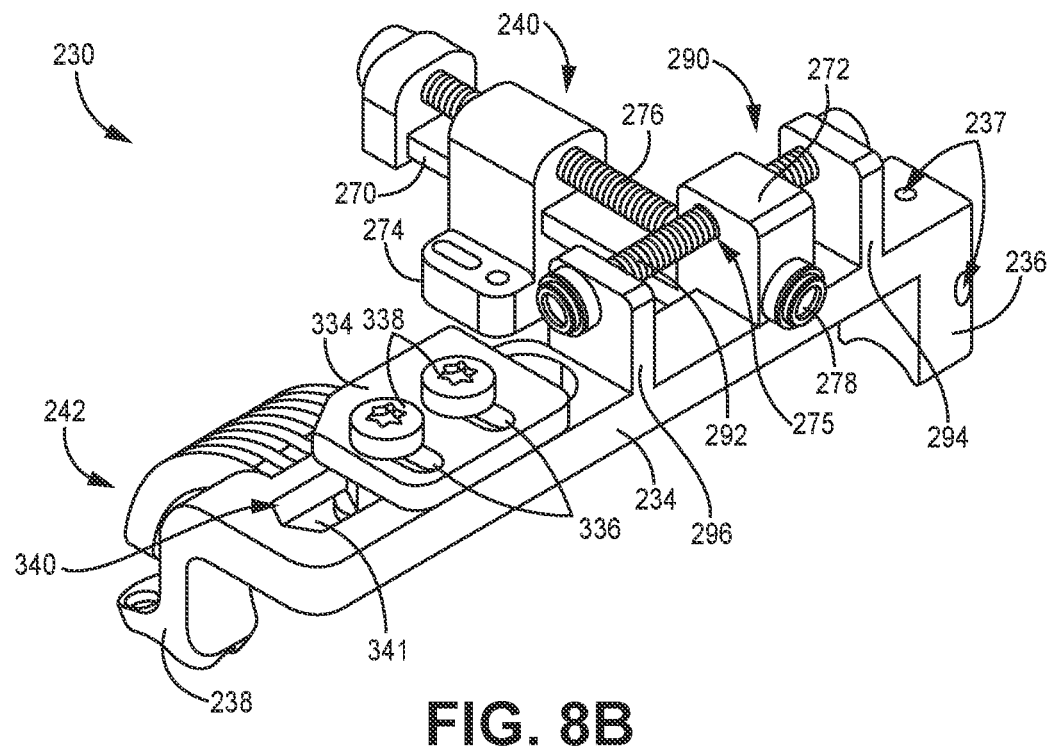
FIG. 8B is a perspective view of a lateral side of the bone deformity correction device of FIG. 8A, according to another embodiment.
Figure 8C:
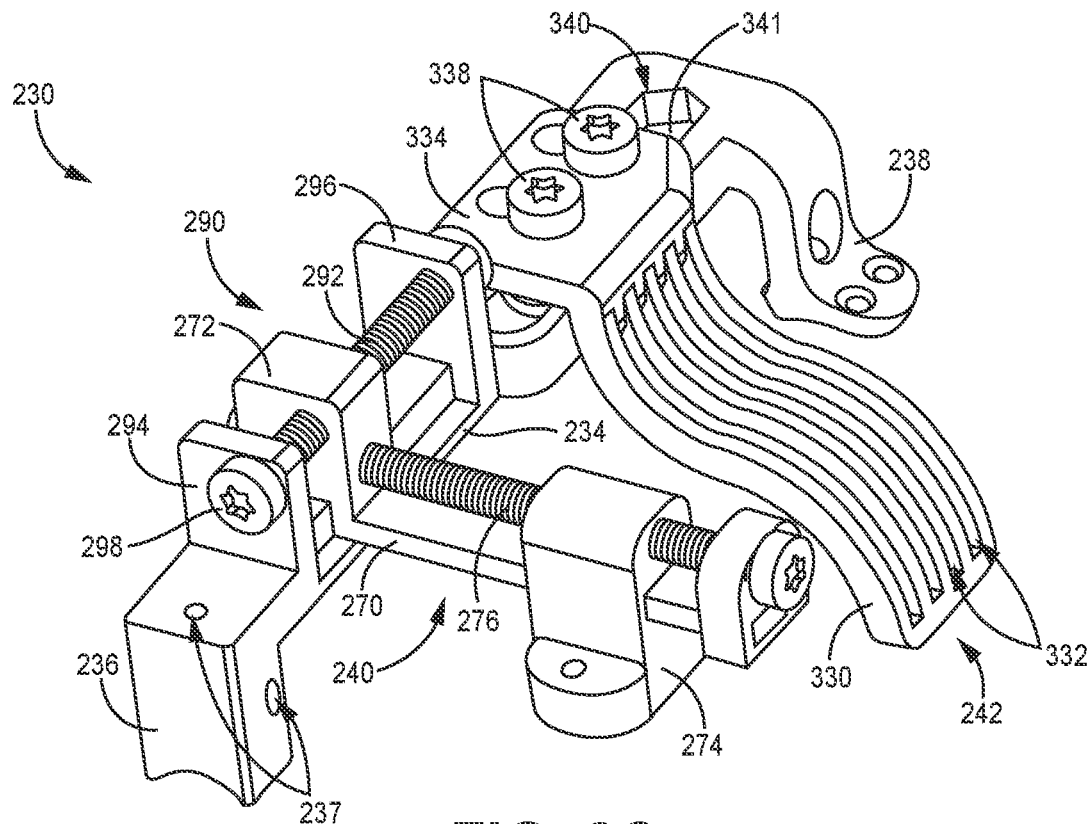
FIG. 8C is another perspective view of the bone deformity correction device of FIG. 8A, according to another embodiment.
Figure 8D:
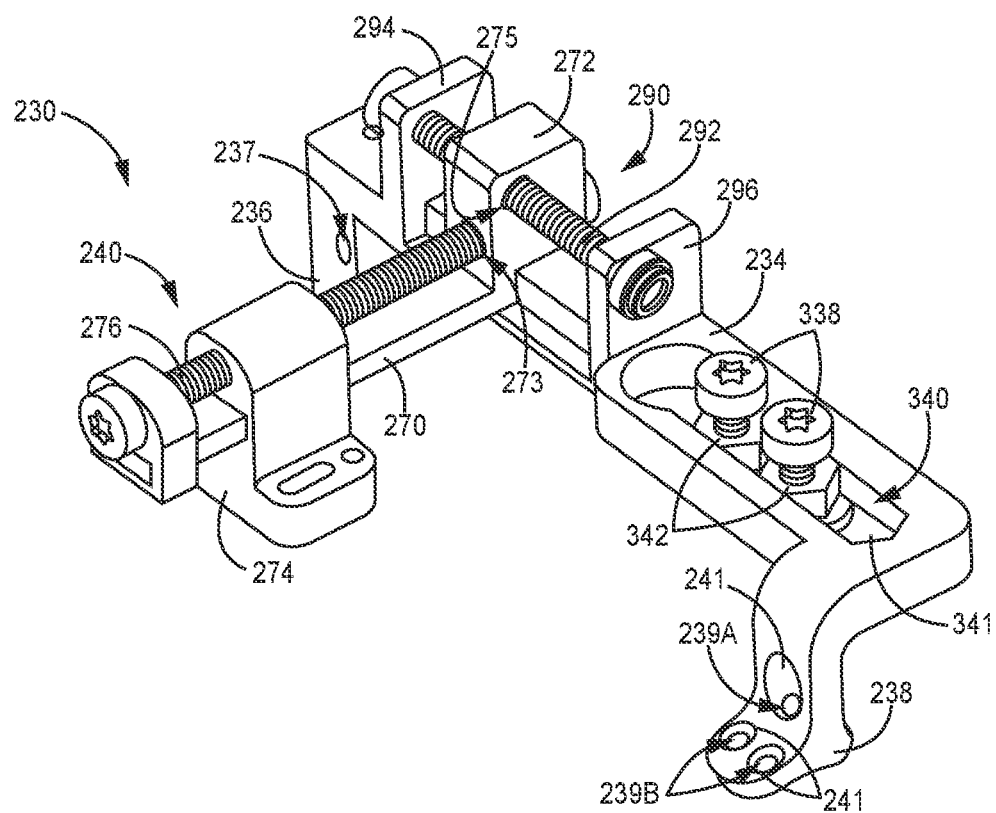
FIG. 8D is a another perspective view of the bone deformity correction device of FIG. 8A with the bone saw guide removed, according to another embodiment.

Similarly, as best shown in FIGS. 8A and 8D, in accordance with one embodiment, the proximal bone attachment structure 238 has three anchor openings defined therein: one larger opening 239A and two smaller openings 239B as shown. The openings 239A, 239B are configured to receive attachment (or "anchor") pins (such as pins 46 discussed above, for example) such that the pins can be positioned through the openings 239A, 239B and into the target bone (such as bone 54 as discussed above) to attach the footing 238 thereto. According to some embodiments, the openings 239A, 239B are disposed at different angles to strengthen the attachment to the target bone when the pins are inserted therethrough. In this specific implementation, the anchor pins (such as pins 46) are standard K wires and the anchor openings 239A, 239B have rounded edges 241 as shown that are shaped to mate with the spheres of the anchor pins (such as the sphere of a commercially available olive wire) such that the anchor pins are more firmly seated within the openings 239A, 239B. More specifically, the round shape of the spheres of the anchor pins can be disposed further into the openings 239A, 239B and with a more secure fit as a result of the rounded edges 219. Alternatively, the openings 239A, 239B can be shaped in any known fashion or have any known features that can provide for a more stable mating with the anchor pins than afforded by an opening without such shaping or feature. Alternatively, the anchor pins (including 46) described herein can be any known elongate anchoring or fixation mechanisms or devices that can be used with bone fixation devices and can mate with the openings 239A, 239B herein. According to certain embodiments, the use of a larger opening 239A to receive a larger pin enhances the stability of the fixation afforded by the larger pin, thereby reducing the number of anchor pins required to attach the proximal footing 238 to the target bone (such as bone 54). Thus, the configuration of the larger opening 239A with the two smaller openings 239B makes it possible to use only two anchor pins: one bigger anchor pin in the larger opening 239A and one smaller pin disposed in one of the two smaller openings 239B. Alternatively, any number of pins can be used. In a further alternative, the proximal footing 238 can have solely the larger anchor opening 239A (and no other openings). In yet another alternate embodiment, the proximal footing 238 can have one, two, four, or any other number of openings of any configuration and any sizes (or a single size).

In the specific exemplary embodiment of FIGS. 8A-8D, the device 230 does not have an extendable arm equivalent to the arm 60 described above with respect to the device 30. More specifically, in this implementation, the distal footing 236 is fixedly attached to the elongate body 36 such that the footing 236 is not adjustable in relation to the body 36. Alternatively, the device 230 can have an extendable arm.

The manipulation arm 240 in this implementation is an adjustable length arm 240 that has a support arm 270 with an attachment block or coupling block (also referred to herein as a "coupling structure") 272 at the first end and an extendable footing 274 slidably disposed at the second end. The manipulation arm 240 also has a rotatable threaded rod 276 that is disposed parallel to the support arm 270 and is rotatably disposed within a first (or lower) lumen 273 defined in the coupling structure 272 at the first end of the rod 276 and is rotatably disposed within the extendable bone attachment structure 274 at the second end. At its first end, the rod 276 has a knob 278 (as best shown in FIG. 8B) such that the rod 276 extends through the first lumen 273 defined in the attachment block 272 and a user can turn the knob 278 to turn the rotatable rod 276. The rod 276 is not threadably coupled to the attachment block 272 within the lumen 273 and thus can easily rotate in relation to the block 272. At its second end, the rod 276 is threadably coupled to the extendable footing 274 in a fashion similar to the rod 76 and the footing 74 discussed in detail above such that rotation of the rod 276 causes the footing 274 to be urged along the length of the rod 276.

In addition, according to this specific exemplary embodiment, the manipulation arm 240 is slidably disposed on the elongate body 234 via an axial adjustment mechanism 290. In this implementation, the axial adjustment mechanism 290 includes a threaded, rotatable rod 292 to which the manipulation arm 240 is attached via the attachment block 272 such that rotation of the rod 292 causes movement of the manipulation arm 240 along the length of the elongate body 234. The coupling structure 272 has a second lumen 275 defined therein that is transverse to the first lumen 273 as shown. More specifically, the second lumen 275 has an axis that is parallel to (and concentric with) the axis of the rotatable rod 292, while the first lumen 273 has an axis that is transverse to the second lumen 275 and is parallel to (and concentric with) the axis of the rotatable rod 276 of the manipulation arm 240. The rotatable rod 292 of the axial adjustment mechanism 290 is rotatably disposed through the second lumen 275. Further, the external threads on the rod 292 are mateable with threads (not shown) defined in the inner surface of the second lumen 275 such that rotation of the rod 292 causes movement of the attachment block 272 along the axis of the rod 292 (and thereby along the length of the elongate body). Thus, rotation of the knob 298 by a user (such as a surgeon) causes the rod 292 to rotate, thereby causing the attachment block 272 to move along the length of the rod 292. Rotation of the rod 292 in one direction causes the block 272 (and thus the arm 240) to move in one direction along the rod 92, while rotation of the rod 292 in the other direction causes the block 272 (and thus the arm 240) to move in the other direction along the rod 292.

Alternatively, one of ordinary skill in the art would understand that the axial adjustment mechanism 290 can be any known mechanism or have any known configuration and can have any known components/features that provide for moving the manipulation arm 240 axially along the length of the rod 292 and further that the manipulation arm 240 can be any known mechanism or have any known configuration and can have any known components/features that provide for urging the footing 274 toward or away from the elongate body 234.

As mentioned above, the device 30 also has an adjustable blade guide 242 that is removably attachable to the body 234 as best shown in FIGS. 8A, 8B, and 8C. The guide 242 has a guide body 330 with two or more slots 332 defined therein, wherein each of the slots 332 can receive and guide a saw blade for use in resection of the target bone (as will be discussed in further detail below). The guide 242 also has an attachment body 334 attached to the guide body 330 that has at least two elongate openings 336 defined therein that can receive at least two lockable bolts 338 that can be disposed therethrough. Further, the elongate body 334 has a slot (or "notch") 340 defined therein that can receive the lockable bolts 338 as best shown in FIG. 8D (in which the guide 242 has been removed), such that the bolts 338 are disposed through the guide openings 336 and into the slot 340. In this specific implementation, the slot 340 is defined in the body 234 such that the slot 340 has a floor or bottom surface 341 as shown. Thus, the bolts 338 are disposed within the slot 340 such that they are in contact with the bottom surface 341 of the slot 340. More specifically, as best shown in FIG. 8D, each of the lockable bolts 338 has a lockable nut 342 rotatably attached thereto and disposed within the slot 340 such that the bolts 338 are attached to and can either be loosened or locked in place via the nuts 342. That is, the nuts 342 are disposed within the slot 340 such that the nuts 342 cannot rotate, thereby allowing for the bolts 338 to be rotated by a user to tighten or loosen the bolts 338 in relation to the nuts 342 Further, the nuts 342 have lips 343 that extend beyond the outer diameter of the nuts 342 along one side thereof, such that the lips 343 can engage with a side of the slot 340 or additional slots therein to retain the nuts 342 within the slot 340. Thus, rotation of the bolts 338 in one direction can loosen the bolts 338 and thereby loosen the guide attachment body 334 such that the guide 342 can be moved axially along the length of the slot 340 or transversely along the length of the elongate openings 336, thereby allowing for positioning the guide 342 in relation to the target bones (like bones 50, 54 as discussed above) for resection as will be discussed in further detail below. Alternatively, the guide 242 can be adjustably coupled to the body 234 via any known mechanism or configuration and can have any known components/features that provide for adjustable and removable coupling to the body 234.

In use, the device 330 can be used in generally the same fashion as the device 30 above as described in detail above to perform a procedure to treat a bone deformity, as best shown in FIGS. 4A-5C.

Although the various embodiments have been described with reference to preferred implementations, persons skilled in the art will recognize that changes may be made in form and detail without departing from the spirit and scope thereof.

What is claimed is:

1. A bone deformity correction device comprising:
    (a) an elongate body comprising:
        (i) a distal bone attachment structure; and
        (ii) a proximal bone attachment structure;
    (b) an adjustable manipulation arm movably coupled to the elongate body, wherein the adjustable manipulation arm is configured to move axially and laterally;
    (c) a cutting guide removably attachable to the elongate body, the cutting guide comprising:
        (i) a guide body comprising at least two saw blade slots defined therein; and
        (ii) a guide attachment body coupleable with the elongate body, the guide attachment body comprising at least two elongate slots defined within the guide attachment body; and
    (d) at least two attachment bolts slidably coupled to the elongate body, wherein each of the at least two attachment bolts is slidably disposed within one of the at least two elongate slots.

2. The bone deformity correction device of claim 1, further comprising an axial adjustment mechanism associated with the elongate body, wherein the adjustable manipulation arm is moveably coupled to the axial adjustment mechanism.

3. The bone deformity correction device of claim 2, wherein the axial adjustment mechanism comprises:
    (a) a threaded axial adjustment rod rotatably coupled to the elongate body; and
    (b) a coupling structure rotatably coupled to the threaded axial adjustment rod, wherein the adjustable manipulation arm is moveably coupled to the coupling structure.

4. The bone deformity correction device of claim 3, wherein the adjustable manipulation arm comprises a threaded manipulation arm rod rotatably coupled to the coupling structure.

5. The bone deformity correction device of claim 4, wherein the coupling structure comprises a first lumen configured to receive the threaded axial adjustment rod and a second lumen configured to receive the threaded manipulation arm rod.

6. The bone deformity correction device of claim 5, wherein the first lumen has an axis that is transverse to an axis of the second lumen.

7. The bone deformity correction device of claim 1, further comprising an elongate slot defined in the elongate body, wherein the cutting guide is slidably coupleable with the elongate body at the elongate slot.

8. (Currently Amened) A bone deformity correction system, comprising:
    (a) a bone deformity correction device comprising:
        (i) an elongate body;
        (ii) an adjustable manipulation arm movably coupled to the elongate body, wherein the adjustable manipulation arm is configured to move axially and laterally; and
        (iii) a cutting guide removably attachable to the elongate body, the cutting guide comprising:
            (1) a guide body comprising at least two saw blade slots defined therein; and
            (2) a guide attachment body coupleable with the elongate body, the guide attachment body comprising at least two elongate slots defined within the guide attachment body; and
            (iv) at least two attachment bolts slidably coupled to the elongate body, wherein each of the at least two attachment bolts is slidably disposed within one of the at least two elongate slots; and
    (b) a fixation plate comprising
        (i) four elongate structures coupled together to form a plate body; and
        (ii) at least two openings defined within the plate body.

9. The bone deformity correction system of claim 8, wherein the elongate device body comprises:
    (a) a distal bone attachment structure; and
    (b) a proximal bone attachment structure.

10. The bone deformity correction system of claim 8, wherein the plate body comprises two extension structures extending from the plate body.

11. The bone deformity correction system of claim 8, wherein a longitudinal axis of the adjustable manipulation arm is transverse to a longitudinal axis of the elongate device body.

12. A bone deformity correction device comprising:
    (a) an elongate body comprising:
        (i) a distal bone attachment structure; and
        (ii) a proximal bone attachment structure; and
        (iii) an elongate slot defined in the elongate body;

(b) an axial adjustment mechanism associated with the elongate body, the axial adjustment mechanism comprising:
  (i) a threaded axial adjustment rod rotatably coupled to the elongate body; and
  (ii) a coupling structure rotatably coupled to the threaded axial adjustment rod;
(c) an adjustable manipulation arm coupled to the coupling structure, the arm comprising:
  (i) a threaded manipulation arm rod rotatably coupled to the coupling structure; and
  (ii) an extendable attachment structure rotatably coupled to the threaded manipulation arm rod; and
(d) a cutting guide removably attachable to the elongate body such that the cutting guide is slidably coupleable with the elongate body at the elongate slot.

13. The bone deformity correction device of claim 12, wherein a longitudinal axis of the adjustable manipulation arm is transverse to a longitudinal axis of the elongate body.

14. The bone deformity correction device of claim 12, wherein the coupling structure comprises a first lumen configured to receive the threaded axial adjustment rod and a second lumen configured to receive the threaded manipulation arm rod.

15. The bone deformity correction device of claim 14, wherein the first lumen has an axis that is transverse to an axis of the second lumen.

16. The bone deformity correction device of claim 12, wherein the cutting guide comprises:
  (a) a guide body comprising at least two saw blade slots defined therein; and
  (b) a guide attachment body coupleable with the elongate body.

* * * * *